(12) United States Patent
Kortenbach et al.

(10) Patent No.: US 7,833,167 B2
(45) Date of Patent: *Nov. 16, 2010

(54) PROXIMAL ACTUATION HANDLE FOR A BIOPSY FORCEPS INSTRUMENT HAVING IRRIGATION AND ASPIRATION CAPABILITIES

(75) Inventors: Juergen Andrew Kortenbach, Miami Springs, FL (US); Vincent Turturro, Miramar, FL (US)

(73) Assignee: Boston Scientific Miami Corporation, Miami, FL (US)

( * ) Notice: Subject to any disclaimer, the term of this patent is extended or adjusted under 35 U.S.C. 154(b) by 271 days.

This patent is subject to a terminal disclaimer.

(21) Appl. No.: 11/725,549

(22) Filed: Mar. 20, 2007

(65) Prior Publication Data
US 2007/0270709 A1 Nov. 22, 2007

Related U.S. Application Data

(60) Continuation of application No. 10/885,021, filed on Jul. 7, 2004, now Pat. No. 7,204,811, which is a continuation of application No. 10/228,278, filed on Aug. 27, 2002, now Pat. No. 6,832,990, which is a continuation of application No. 09/599,403, filed on Jun. 22, 2000, now Pat. No. 6,544,194, which is a division of application No. 08/794,352, filed on Feb. 3, 1997, now Pat. No. 6,142,956, which is a continuation-in-part of application No. 08/756,260, filed on Nov. 25, 1996, now Pat. No. 5,897,507.

(51) Int. Cl.
*A61B 10/00* (2006.01)

(52) U.S. Cl. .................................. 600/564

(58) Field of Classification Search ......... 600/562–570, 600/153, 121, 123, 127, 156, 114, 101, 104; 606/127, 170, 205, 184
See application file for complete search history.

(56) References Cited

U.S. PATENT DOCUMENTS 2,708,437 A 5/1955 Hutchins
3,093,925 A * 6/1963 Greene ........................ 446/18

(Continued)

FOREIGN PATENT DOCUMENTS

EP 0 317 526 A1 5/1989

(Continued)

OTHER PUBLICATIONS

Notice of Reasons for Rejection mailed Sep. 12, 2006 in Japanese Patent Application No. 10-526709.

(Continued)

*Primary Examiner*—Max Hindenburg
*Assistant Examiner*—Brian Szmal
(74) *Attorney, Agent, or Firm*—Finnegan, Henderson, Farabow, Garrett & Dunner LLP

(57) ABSTRACT

An embodiment of the invention includes a medical device. The device includes a proximal handle coupled to the proximal end of an elongated member, and a distal assembly coupled to the distal end of the elongated member. The device also includes a collar coupled to the distal assembly proximate to the distal assembly. The collar is adapted to couple the distal assembly to a medical instrument.

9 Claims, 18 Drawing Sheets

U.S. PATENT DOCUMENTS

| | | |
|---|---|---|
| 3,173,414 A | 3/1965 | Guillant |
| 3,289,669 A | 12/1966 | Dwyer et al. |
| 3,401,684 A | 9/1968 | Dremann |
| 3,590,808 A | 7/1971 | Muller |
| 3,732,858 A | 5/1973 | Banko |
| 3,964,468 A | 6/1976 | Schulz |
| 3,980,086 A | 9/1976 | Kletschka et al. |
| 3,989,033 A | 11/1976 | Halpern et al. |
| 3,989,049 A | 11/1976 | Yoon |
| 3,992,565 A | 11/1976 | Gatfield |
| 4,014,333 A | 3/1977 | McIntyre |
| 4,200,111 A | 4/1980 | Harris |
| 4,282,884 A | 8/1981 | Boebel |
| 4,315,509 A | 2/1982 | Smit |
| 4,445,517 A | 5/1984 | Feild |
| 4,519,385 A | 5/1985 | Atkinson et al. |
| 4,522,206 A | 6/1985 | Whipple et al. |
| 4,617,013 A | 10/1986 | Betz |
| 4,632,110 A | 12/1986 | Sanagi |
| 4,644,951 A | 2/1987 | Bays |
| 4,646,751 A | 3/1987 | Maslanka |
| 4,651,753 A | 3/1987 | Lifton |
| 4,662,371 A | 5/1987 | Whipple et al. |
| 4,681,123 A | 7/1987 | Valtchev |
| 4,693,257 A | 9/1987 | Markham |
| 4,712,545 A | 12/1987 | Honkanen |
| 4,759,349 A | 7/1988 | Betz et al. |
| 4,763,668 A | 8/1988 | Macek et al. |
| 4,776,840 A | 10/1988 | Freitas et al. |
| 4,785,825 A | 11/1988 | Romaniuk et al. |
| 4,881,550 A | 11/1989 | Kothe |
| 4,909,782 A | 3/1990 | Semm et al. |
| 4,919,152 A | 4/1990 | Ger |
| 4,924,851 A | 5/1990 | Ognier et al. |
| RE33,258 E | 7/1990 | Onik et al. |
| 4,944,093 A | 7/1990 | Falk |
| 4,950,278 A | 8/1990 | Sachse et al. |
| 4,953,559 A | 9/1990 | Salerno |
| 4,966,162 A | 10/1990 | Wang |
| 4,971,067 A | 11/1990 | Bolduc et al. |
| 4,973,311 A | 11/1990 | Iwakoshi et al. |
| 4,976,723 A | 12/1990 | Schad |
| 4,986,825 A | 1/1991 | Bays et al. |
| 5,035,688 A | 7/1991 | Inui |
| 5,082,000 A | 1/1992 | Picha et al. |
| 5,085,658 A | 2/1992 | Meyer |
| 5,106,364 A | 4/1992 | Hayafuji et al. |
| 5,112,346 A | 5/1992 | Hiltebrandt et al. |
| 5,125,910 A | 6/1992 | Freitas |
| 5,147,292 A | 9/1992 | Kullas et al. |
| 5,152,780 A | 10/1992 | Honkanen et al. |
| 5,160,319 A | 11/1992 | Emery et al. |
| 5,160,343 A | 11/1992 | Brancel et al. |
| 5,171,255 A | 12/1992 | Rydell |
| 5,172,700 A | 12/1992 | Bencini et al. |
| 5,176,629 A | 1/1993 | Kullas et al. |
| 5,186,714 A | 2/1993 | Boudreault et al. |
| 5,195,533 A | 3/1993 | Chin et al. |
| 5,195,958 A | 3/1993 | Phillips |
| 5,195,959 A | 3/1993 | Smith |
| 5,197,963 A | 3/1993 | Parins |
| 5,197,968 A | 3/1993 | Clement |
| 5,209,747 A | 5/1993 | Knoepfler |
| 5,217,460 A | 6/1993 | Knoepfler |
| 5,219,357 A | 6/1993 | Honkanen et al. |
| 5,230,704 A | 7/1993 | Moberg et al. |
| 5,244,459 A | 9/1993 | Hill |
| 5,250,056 A | 10/1993 | Hasson |
| 5,251,641 A | 10/1993 | Xavier |
| 5,285,795 A | 2/1994 | Ryan et al. |
| 5,286,255 A | 2/1994 | Weber |
| 5,300,087 A | 4/1994 | Knoepfler |
| 5,312,327 A | 5/1994 | Bales et al. |
| 5,312,400 A | 5/1994 | Bales et al. |
| 5,314,406 A | 5/1994 | Arias et al. |
| 5,318,528 A | 6/1994 | Heaven et al. |
| 5,320,627 A | 6/1994 | Sorenson et al. |
| 5,325,866 A | 7/1994 | Krzyzanowski |
| 5,336,238 A | 8/1994 | Holmes et al. |
| 5,344,428 A | 9/1994 | Griffiths |
| 5,409,008 A | 4/1995 | Svenson et al. |
| 5,419,774 A | 5/1995 | Willard et al. |
| 5,431,645 A | 7/1995 | Smith et al. |
| 5,456,689 A | 10/1995 | Kresch et al. |
| 5,471,992 A | 12/1995 | Banik et al. |
| 5,503,616 A * | 4/1996 | Jones .................. 600/153 |
| 5,505,210 A | 4/1996 | Clement |
| 5,526,822 A | 6/1996 | Burbank et al. |
| 5,527,331 A | 6/1996 | Kresch et al. |
| 5,527,332 A | 6/1996 | Clement |
| 5,538,008 A | 7/1996 | Crowe |
| 5,542,432 A | 8/1996 | Slater et al. |
| 5,551,448 A | 9/1996 | Matula et al. |
| 5,562,102 A | 10/1996 | Taylor |
| 5,562,640 A | 10/1996 | McCabe et al. |
| 5,569,299 A | 10/1996 | Dill et al. |
| 5,573,008 A | 11/1996 | Robinson et al. |
| 5,575,293 A | 11/1996 | Miller et al. |
| 5,593,416 A | 1/1997 | Donahue |
| 5,595,185 A | 1/1997 | Erlich |
| 5,601,572 A | 2/1997 | Middleman et al. |
| 5,601,585 A | 2/1997 | Banik et al. |
| 5,601,601 A | 2/1997 | Tal et al. |
| 5,603,724 A | 2/1997 | O'Connor |
| 5,607,391 A | 3/1997 | Klinger et al. |
| 5,620,415 A | 4/1997 | Lucey et al. |
| 5,636,639 A | 6/1997 | Turturro et al. |
| 5,638,827 A | 6/1997 | Palmer et al. |
| 5,645,075 A | 7/1997 | Palmer et al. |
| 5,649,547 A | 7/1997 | Ritchart et al. |
| 5,674,183 A | 10/1997 | Adachi |
| 5,683,359 A | 11/1997 | Farkas et al. |
| 5,683,388 A | 11/1997 | Slater et al. |
| 5,715,832 A | 2/1998 | Koblish et al. |
| 5,775,333 A | 7/1998 | Burbank et al. |
| 5,779,648 A | 7/1998 | Banik et al. |
| 5,810,876 A | 9/1998 | Kelleher |
| 5,817,013 A * | 10/1998 | Ginn et al. .................. 600/114 |
| 5,823,971 A | 10/1998 | Banik et al. |
| 5,840,044 A | 11/1998 | Dassa et al. |
| 5,871,453 A | 2/1999 | Banik et al. |
| 5,893,876 A * | 4/1999 | Turkel et al. ................. 606/205 |
| 5,897,507 A * | 4/1999 | Kortenbach et al. ......... 600/562 |
| 5,928,164 A | 7/1999 | Burbank et al. |
| 5,961,534 A | 10/1999 | Banik et al. |
| 5,980,469 A | 11/1999 | Burbank et al. |
| 6,017,316 A | 1/2000 | Ritchart et al. |
| 6,032,673 A | 3/2000 | Savage et al. |
| 6,053,877 A | 4/2000 | Banik et al. |
| 6,142,956 A | 11/2000 | Kortenbach et al. |
| 6,142,957 A | 11/2000 | Diamond et al. |
| 6,428,486 B2 | 8/2002 | Ritchart et al. |
| 6,544,194 B1 | 4/2003 | Kortenbach et al. |
| 2001/0007925 A1 | 7/2001 | Ritchart et al. |
| 2002/0016555 A1 | 2/2002 | Ritchart et al. |
| 2002/0120212 A1 | 8/2002 | Ritchart et al. |
| 2004/0019299 A1 | 1/2004 | Ritchart et al. |
| 2006/0167377 A1 | 7/2006 | Ritchart et al. |

FOREIGN PATENT DOCUMENTS

| | | |
|---|---|---|
| EP | 0 526 115 A1 | 2/1993 |
| EP | 0 890 339 A1 | 1/1999 |
| JP | 59-186548 A | 10/1984 |

| | | | |
|---|---|---|---|
| JP | S62-164010 U | 10/1987 | |
| JP | H01-157714 U | 10/1989 | |
| JP | 03-003311 A | 1/1991 | |
| JP | 04-135554 A | 5/1992 | |
| JP | 06-054853 A | 3/1994 | |
| JP | H06-503502 A | 4/1994 | |
| JP | H09-503404 A | 4/1997 | |
| JP | H09-503942 A | 4/1997 | |
| JP | H09-510638 A | 10/1997 | |
| WO | WO 92/07516 A1 | 5/1992 | |
| WO | WO 93/07917 A1 | 4/1993 | |
| WO | WO 95/08945 A2 | 4/1995 | |
| WO | WO 95/10981 A1 | 4/1995 | |
| WO | WO 95/25465 A2 | 9/1995 | |
| WO | WO 96/22056 A1 | 7/1996 | |

OTHER PUBLICATIONS 510k application communications between Department of Health & Human Services and William Z. Kolozsi, M.D., relating to Triton Technologies Multiple Biopsy Device, dated Mar. 11, 1991 through May 1, 1991, 27 pages.

Japanese Unexamined Patent Publication (Kokai) No. 07-111974, published May 2, 1995.

English language translation of Official Action from Japanese Patent Office for Patent Application No. 10-533117, dated Apr. 2, 2002.

Quinton, "Model 4.7mm Multipurpose Biopsy Tube" operator manual, 10 pages.

* cited by examiner

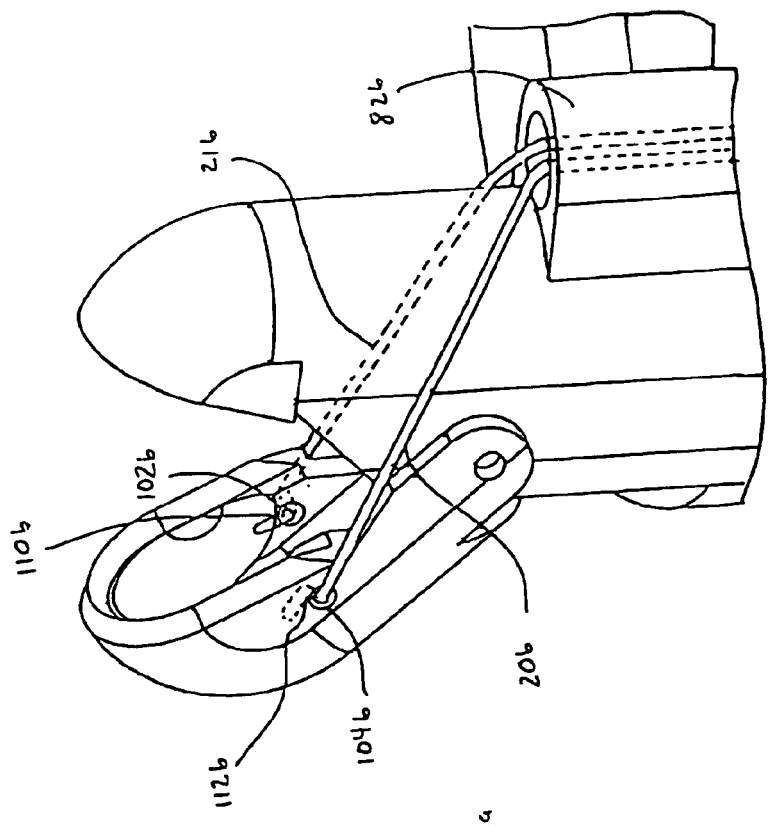
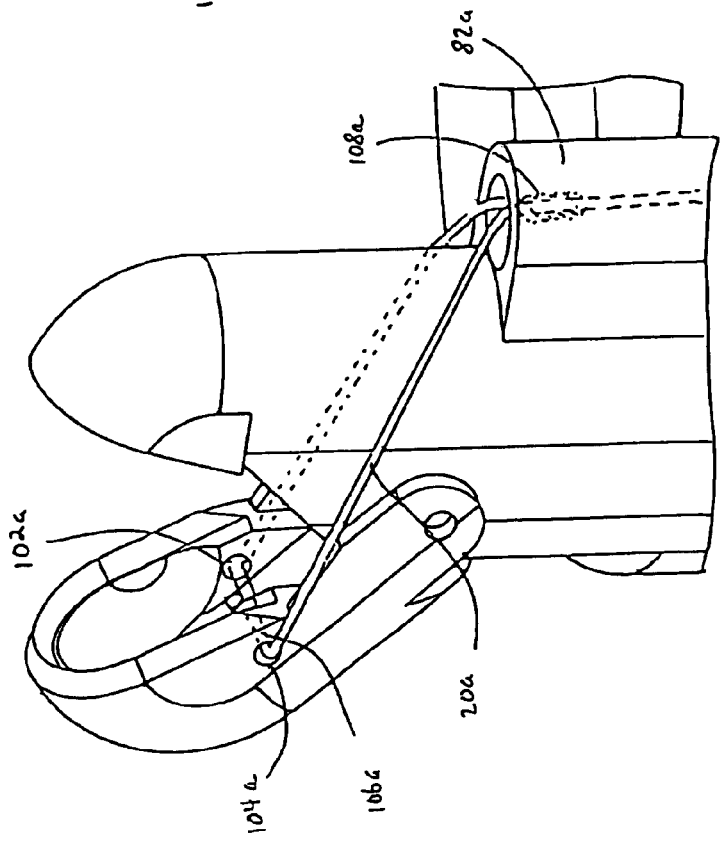

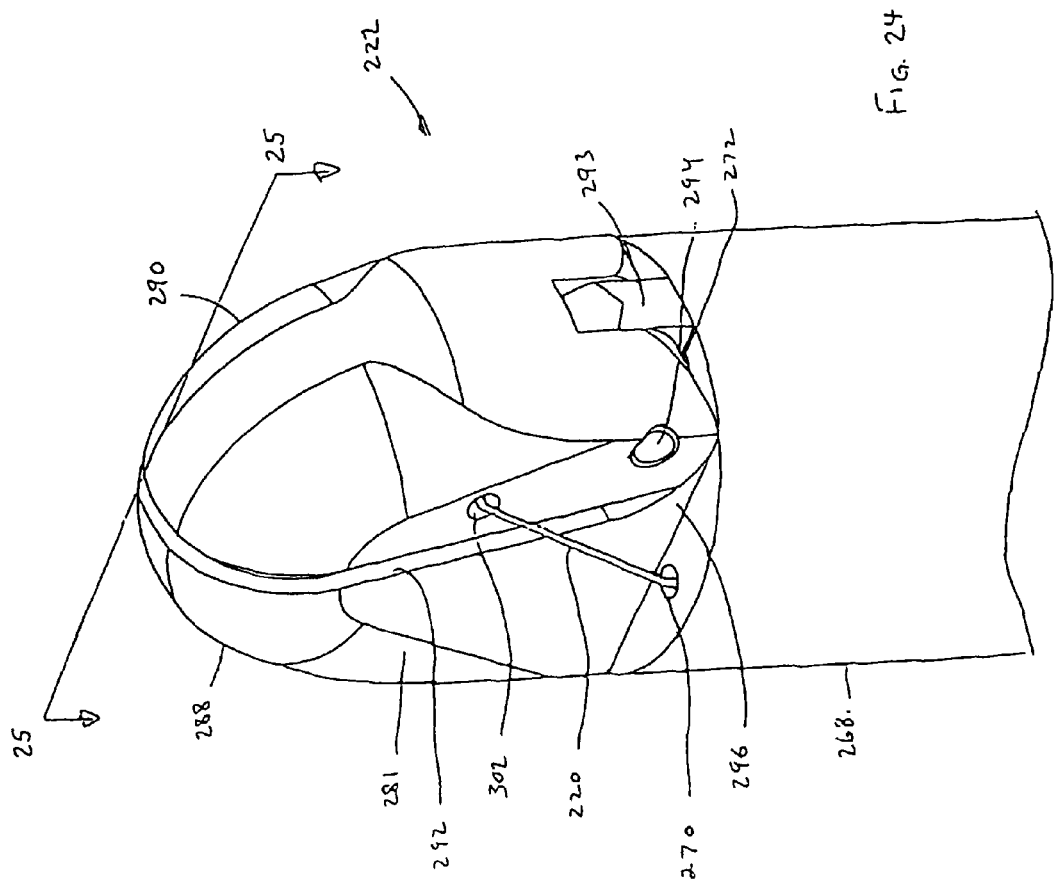

PROXIMAL ACTUATION HANDLE FOR A BIOPSY FORCEPS INSTRUMENT HAVING IRRIGATION AND ASPIRATION CAPABILITIES

This application is a continuation of application Ser. No. 10/885,021, filed Jul. 7, 2004 now U.S. Pat. No. 7,204,811, of Juergen Andrew KORTENBACH et al. for Proximal Actuation Handle For A Biopsy Forceps Instrument Having Irrigation And Aspiration Capabilities, currently pending, which is a continuation of application Ser. No. 10/228,278, filed Aug. 27, 2002 (now U.S. Pat. No. 6,832,990); which is a continuation of application Ser. No. 09/599,403, filed Jun. 22, 2000 (now U.S. Pat. No. 6,544,194); which is a divisional of application Ser. No. 08/794,352, filed Feb. 3, 1997 (now U.S. Pat. No. 6,142,956); which is a continuation-in-part of application Ser. No. 08/756,260, filed Nov. 25, 1996 (now U.S. Pat. No. 5,897,507), all of which are hereby incorporated by reference in their entirety herein.

BACKGROUND OF THE INVENTION

1. Field of the Invention

This invention relates broadly to endoscopic surgical instruments. More particularly, this invention relates to an actuation handle for an endoscopic biopsy forceps instrument with means for facilitating sample removal without withdrawal of the biopsy forceps instrument from an endoscope.

2. State of the Art

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome typically includes a long flexible coil having a pair of opposed jaws at the distal end and manual actuation means at the proximal end. Manipulation of the actuation means opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site. While viewing the biopsy site through the fiber optics of the endoscope, the surgeon positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

A biopsy tissue sampling procedure often requires the taking of several tissue samples either from the same or from different biopsy sites. Unfortunately, most bioptomes are limited to taking a single tissue sample, after which the device must be withdrawn from the endoscope and the tissue collected before the device can be used again to take a second tissue sample. Several attempts have been made to provide an instrument which will allow the taking of several tissue samples before the instrument must be withdrawn and the samples collected. Problems in providing such an instrument include the extremely small size required by the narrow lumen of the endoscope and the fact that the instrument must be flexible in order to be inserted through the lumen of the endoscope. Thus, several known multiple sample biopsy instruments are precluded from use with an endoscope because of their size and rigidity. These include the "punch and suction type" instruments disclosed in U.S. Pat. No. 3,989,033 to Halpern et al. and U.S. Pat. No. 4,522,206 to Whipple et al. Both of these devices have a hollow tube with a punch at the distal end and a vacuum source coupled to the proximal end. A tissue sample is cut with the punch and suctioned away from the biopsy site through the hollow tube. It is generally recognized, however, that dry suctioning tissue samples (i.e., without the use of an irrigating fluid) through a long narrow flexible bioptome is virtually impossible.

Efforts have been made to provide multiple sampling ability to an instrument which must traverse the narrow lumen of an endoscope. These efforts have concentrated on providing a cylindrical storage space at the distal end of the instrument wherein several tissue samples can be accumulated before the instrument is withdrawn from the endoscope. U.S. Pat. No. 4,651,753 to Lifton, for example, discloses a rigid cylindrical member attached to the distal end of a first flexible tube. The cylindrical member has a lateral opening and a concentric cylindrical knife blade is slidably mounted within the cylindrical member. A second flexible tube, concentric to the first tube is coupled to the knife blade for moving the knife blade relative to the lateral opening in the cylindrical member. A third flexible tube having a plunger tip is mounted within the second flexible tube and a vacuum source (a syringe) is coupled to the proximal end of the third tube. A tissue sample is taken by bringing the lateral opening of the cylindrical member upon the biopsy site, applying vacuum with the syringe to draw tissue into the lateral opening, and pushing the second flexible tube forward to move the knife blade across the lateral opening. A tissue sample is thereby cut and trapped inside the cylindrical knife within the cylindrical member. The third flexible tube is then pushed forward moving its plunger end against the tissue sample and pushing it forward into a cylindrical storage space at the distal end of the cylindrical member. Approximately six samples can be stored in the cylindrical member, after which the instrument is withdrawn from the endoscope. A distal plug on the cylindrical member is removed and the six samples are collected by pushing the third tube so that its plunger end ejects the samples.

The device of the Lifton patent suffers from several recognizable drawbacks. First, it is often difficult to obtain a tissue sample laterally of the device. Second, in order to expedite the obtaining of a lateral sample, a syringe is used to help draw the tissue into the lateral opening. However, this causes what was once a two-step procedure (position and cut), to become a three-step procedure (position, suction, cut). In addition, the use of a syringe requires an additional hand. Third, the Lifton patent adds a fourth step to the biopsy procedure by requiring that the tissue sample be pushed into the storage space. Thus, in all, the Lifton patent requires substantial effort on the part of the surgeon and an assistant and much of this effort is involved in pushing tubes, an action which is counter-intuitive to classical biopsy sampling. The preferred mode of operation of virtually all endoscopic tools is that a gripping action at the distal end of the instrument is effected by a similar action at the proximal end of the instrument. Classical biopsy forceps jaws are closed by squeezing a manual actuation member in a syringe-like manner.

A more convenient endoscopic multiple sample biopsy device is disclosed in U.S. Pat. No. 5,171,255 to Rydell. Rydell provides a flexible endoscopic instrument with a knife-sharp cutting cylinder at its distal end. A coaxial anvil is coupled to a pull wire and is actuated in the same manner as conventional biopsy forceps. When the anvil is drawn into the cylinder, tissue located between the anvil and the cylinder is cut and pushed into a storage space within the cylinder. Several samples may be taken and held in the storage space before the device is withdrawn from the endoscope. While the device of Rydell is effective in providing a multiple sample tool where each sample is obtained with a traditional two-step procedure (position and cut), it is still limited to lateral cutting which is often problematic. Traditional biopsy forceps provide jaws which can grasp tissue frontally or laterally. Even as such, it is difficult to position the jaws about the tissue to be sampled. Lateral sampling is even more difficult.

A multiple sample biopsy forceps of a more traditional form is disclosed in co-owned U.S. Pat. No. 5,542,432 to Slater et al. Slater et al. discloses an endoscopic multiple sample biopsy forceps having a jaw assembly which includes a pair of opposed toothed jaw cups each of which is coupled by a resilient arm to a base member. The base member of the jaw assembly is mounted inside a cylinder and axial movement of one of the jaw assembly and cylinder relative to the other draws the arms of the jaws into the cylinder or moves the cylinder over the arms of the jaws to bring the jaw cups together in a biting action. The arms of the jaws effectively form a storage chamber which extends proximally from the lower jaw cup and prevents accumulated biopsy samples from being squeezed laterally out from between the jaws during repeated opening and closing of the jaws and the lower jaw cup enhances movement of the biopsy samples into the storage chamber. The device can hold up to four samples before it must be retrieved out of the endoscope. However, in some biopsy procedures it is sometimes desirous to retrieve more. In addition, it has been found that samples within the chamber can stick together and make determinations of which sample came from which biopsy site somewhat difficult.

U.S. Pat. No. 5,538,008 to Crowe discloses a multiple sample bioptome which purports to take several samples and to transfer each sample by water pressure through a duct to the proximal end of the instrument, where each sample can be individually retrieved. The device includes a plastic jaw set biased in an open position and coupled to the distal end of an elongate tube, up to seven feet long. The tube defines a duct. A sleeve extends over the tube and a water flow passage is provided between the tube and the sleeve. An aperture is provided in the tube to permit the water flow passage to meet the duct at the distal end of the tube. Withdrawing the tube into the sleeve is disclosed to force the jaws closed and enable a sample to be cut from tissue and lodge in the duct. The water flow passage is disclosed to enable water to flow under pressure from the proximal end of passage to the distal end of the passage, through the aperture and into the distal end of the duct and to be aspirated to the proximal end of the duct, thereby transferring with it any sample contained in the duct to the proximal end where the sample can be retrieved.

While on paper the Crowe device is appealing, in practice the design is impractical and flawed. For example, it would be very difficult, if not impossible, to slide the elongate tube, up to seven feet in length, relative to a sleeve of substantially the same length. It would also be difficult to maintain an unobstructed water flow passage between the tube and sleeve as the tube and sleeve curve and bend through the body. Furthermore, in order for the jaws to cut a tissue sample, the tube and jaws must be drawn into the sleeve, thereby undesirably pulling the jaws away from the tissue to be sampled.

SUMMARY OF THE INVENTION

It is therefore an object of the invention to provide an endoscopic biopsy forceps instrument which permits numerous tissue samples to be taken from a patient without removing the forceps from within the patient.

It is another object of the invention to provide an endoscopic biopsy forceps instrument which can individually retrieve each of several tissue samples from the forceps without removing the forceps from the patient.

It is also an object of the invention to provide an endoscopic biopsy forceps instrument which irrigates the forceps and aspirates tissue samples contained therein.

It is an additional object of the invention to provide an endoscopic biopsy forceps instrument which includes a proximal actuation handle having a chamber to retain tissue samples aspirated through the instrument.

It is a further object of the invention to provide an endoscopic biopsy forceps instrument which includes a proximal actuation handle for an endoscopic biopsy forceps instrument which includes a control means for controlling the aspiration and irrigation of fluid through the instrument.

In accord with these objects which will be discussed in detail below, an endoscopic biopsy forceps instrument is provided and generally includes a proximal actuation handle, a distal forceps assembly, a control member coupled to the proximal actuation handle and the distal forceps assembly, and a flexible multi-lumen tubular member having an irrigation conduit, an aspiration conduit, and a control conduit which receives the control member.

According to a preferred embodiment of the invention, the proximal actuation handle includes a shaft and a spool slidably mounted on the shaft. The actuation handle is also provided with a proximal irrigation passage, a sample chamber, a sample catch member, and a pinch valve which regulates irrigation and aspiration. The proximal irrigation passage is coupled to the irrigation conduit and to an irrigation coupling tube. The sample chamber is coupled to the aspiration conduit and to an aspiration coupling tube. The sample catch member includes a screen which is inserted into the sample chamber and filters out tissue samples from the aspirated fluid. The irrigation coupling tube and the aspiration coupling tube extend through the pinch valve which operates to control the flow of fluid through the tubes. The actuation handle is coupled to the proximal ends of both the flexible tubular member and the control member and moves the control member relative to the tubular member.

The distal assembly is coupled to the distal end of the tubular member and includes a hollow jaw cup coupled over the distal end of the aspiration conduit and a hollow movable jaw pivotally coupled adjacent the irrigation conduit. The jaw cup is preferably formed from a hard plastic and has a blunt cutting surface, while the movable jaw is preferably a metal jaw with a sharp cutting edge. The movable jaw is further coupled to the control member, such that actuation of the actuation handle moves the movable jaw relative to the jaw cup, and thereby moves the jaws from an open position to a closed position. Moving the hollow jaws to a closed position provides a substantially fluidtight coupling between the irrigation and aspiration conduits.

It will be appreciated that the distal end of the instrument is brought into contact with tissue of which a sample is required and the actuation handle is actuated to close the jaws and cut off a tissue sample. With the jaws in a closed position, water is irrigated through the irrigation conduit to the jaws at the distal end of the instrument and aspirated from the jaws to the proximal end of the instrument through the aspiration conduit, such that the sample cut by the jaws is aspirated with the water. As the water is aspirated it passes through the chamber and the sample is filtered onto the screen. The screen may easily be removed to retrieve the sample. It will be further appreciated that the entire procedure of cutting a sample and retrieving the sample may be performed without removing the endoscopic biopsy forceps instrument from its location within the body.

According to one embodiment of the biopsy forceps instrument, the tubular member is ovoid in shape and defines a control conduit, an irrigation conduit, and an aspiration conduit. The distal forceps assembly includes a movable jaw, and a substantially rigid molded collar which is provided with a proximal socket-like coupling means for coupling the tubular member thereto, a fixed jaw cup, a distal irrigation passage, and a control passage. The collar is of similar diameter to the endoscope and is designed to be coupled to the outside of the distal end of an endoscope by a silicone rubber sock. The movable jaw is pivotally mounted on the molded collar and is movable relative to jaw cup. The tubular member is coupled in the socket. A control wire extends through the control conduit and the control passage is coupled to the two holes in the movable jaw.

According to a second embodiment, the biopsy forceps instrument includes a tubular member which defines an aspiration conduit having a circular cross section, an irrigation conduit having a kidney-shaped cross section, and two control conduits. The distal assembly includes a stationary jaw bonded to the distal end of the tubular member, and a movable jaw. The stationary jaw includes a hollow jaw cup, a clevis member and two proximal ramps. The jaw cup is located over the aspiration conduit, and the clevis and the proximal ramps extend from the jaw cup over the irrigation conduit. The movable jaw is coupled to the clevis and is guided along the proximal ramps. The two control conduits exit the distal end of the tubular member lateral of the proximal ramps. A central portion of a control member is coupled to the movable jaw and each end of the control member extends through the control conduits to the proximal end of the instrument.

According to a third embodiment of the biopsy forceps instrument, the instrument includes a tubular member which defines an aspiration conduit having a circular cross section and an irrigation conduit having a crescent-shaped cross section. The distal assembly is substantially similar to the second embodiment. The proximal ramps abut and partially cover the irrigation conduit to define two entrances into the irrigation conduit for the control members. A distal end of each control member is coupled to the movable jaw and the control members extend through the entrances and into the irrigation conduit. The entrances are sufficiently small such that when the jaws are in a closed position and fluid is irrigated through the irrigation conduit to the distal assembly, substantially all of the fluid passes through the irrigation conduit and into the jaws; i.e. only an insubstantial amount of the fluid irrigated through the irrigation conduit exits through the entrances formed by the ramps.

Additional objects and advantages of the invention will become apparent to those skilled in the art upon reference to the detailed description taken in conjunction with the provided figures.

BRIEF DESCRIPTION OF THE DRAWINGS

FIG. 12 is a broken perspective view of the distal assembly of the first embodiment illustrating an alternate control member configuration;

FIG. 13 is a broken perspective view of the distal assembly of the first embodiment illustrating another alternate control member configuration;

FIG. 24 is an enlarged broken perspective view of the distal end of the third embodiment of the invention with the biopsy jaws in a closed position;

DETAILED DESCRIPTION OF THE PREFERRED EMBODIMENTS

Figure 1:
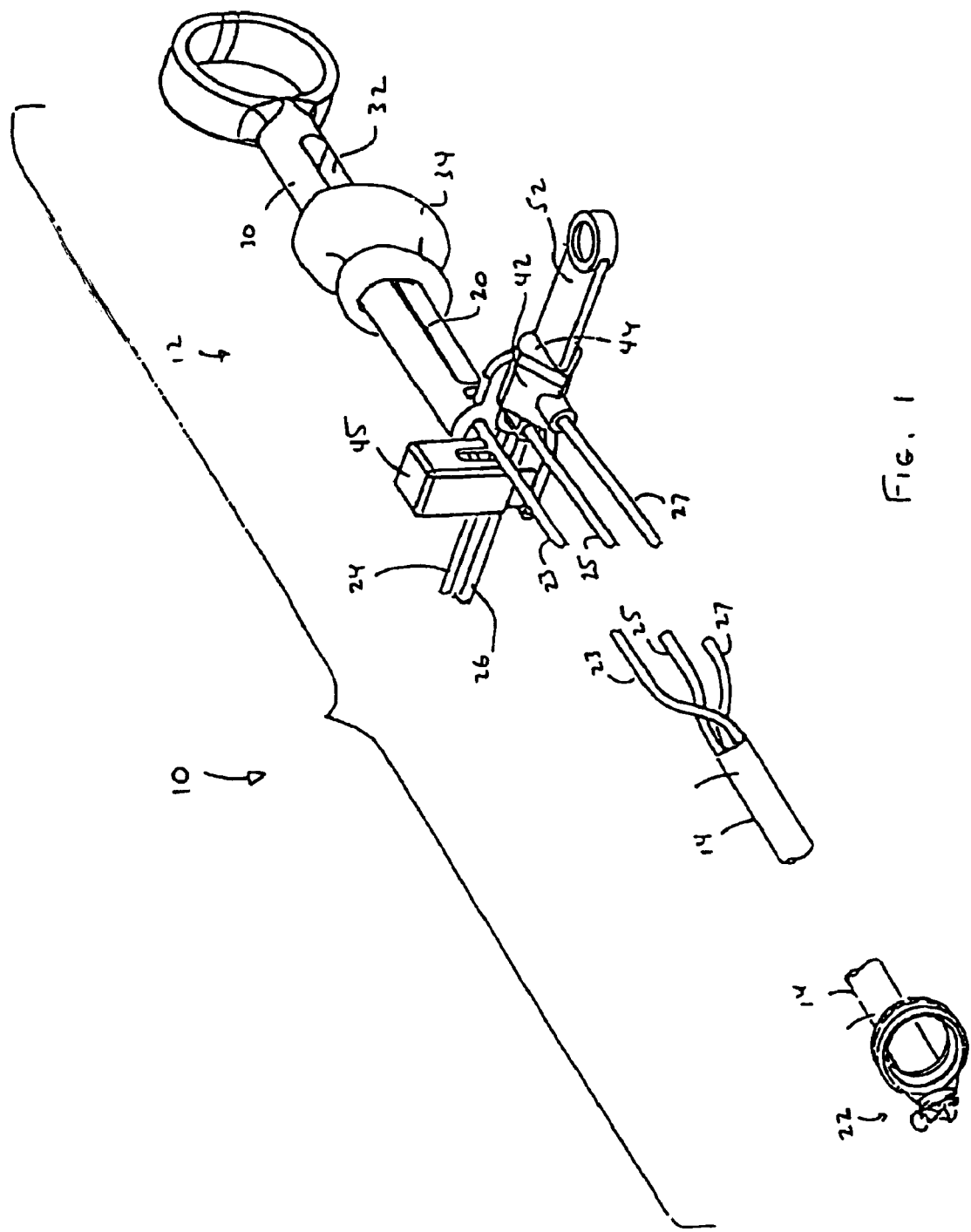
FIG. 1 is a broken perspective view of a first embodiment of an endoscopic biopsy forceps instrument according to the invention.

Turning now to FIG. 1, a multiple sample biopsy forceps instrument 10 is shown. The biopsy forceps instrument generally includes a proximal actuation handle 12, a flexible multi-lumen tubular member 14, a pull wire 20, and a distal assembly 22. Several coupling tubes are preferably provided to couple the proximal actuation handle 12 to the tubular member 14 and to irrigation and aspiration means. In particular, a control coupling tube 23, first and second irrigation coupling tubes 24, 25 and first and second aspiration coupling tubes 26, 27 are provided.

Figure 2:
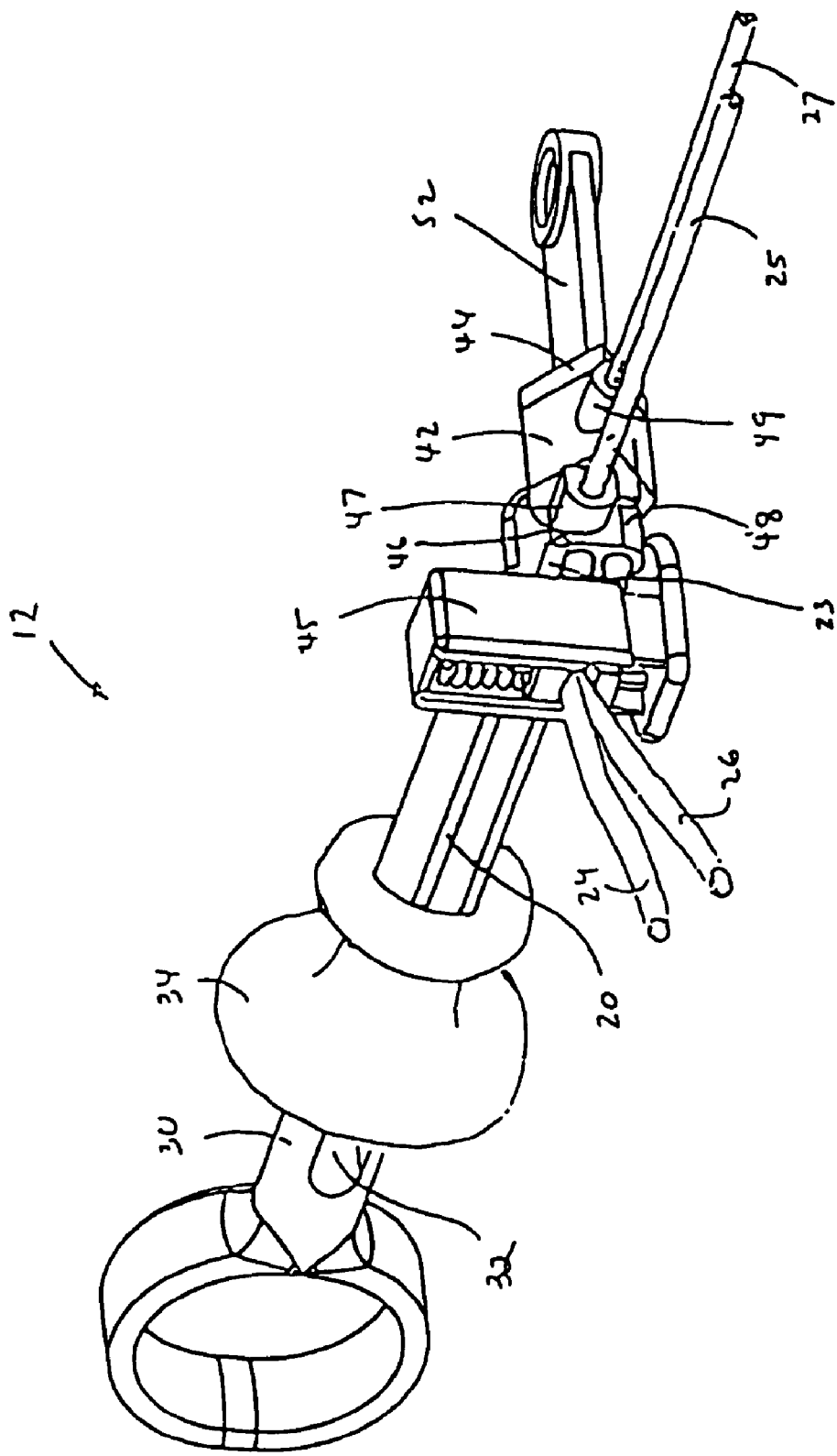
FIG. 2 is a broken perspective view of the proximal end of the first embodiment of the invention.
Figure 4:
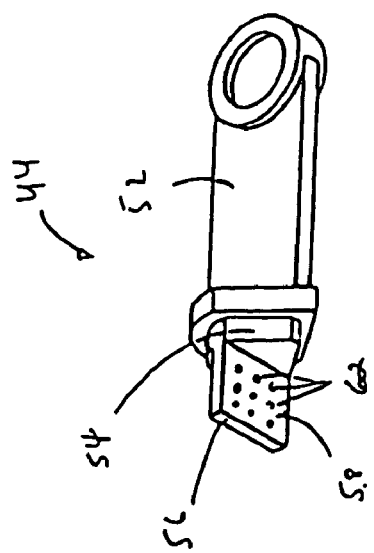
FIG. 4 is a perspective view of the front side of the sample catch member of the first embodiment of the invention.
Figure 5:
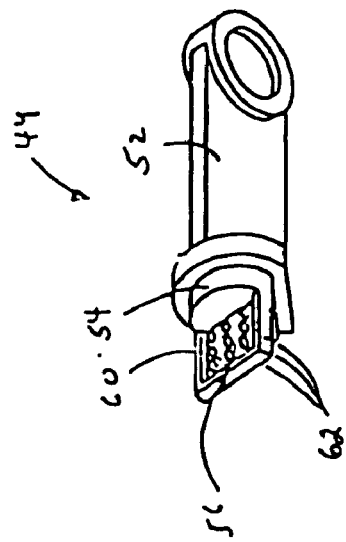
FIG. 5 is a perspective view of the back side of the sample catch member of the first embodiment of the invention.
Figure 3:
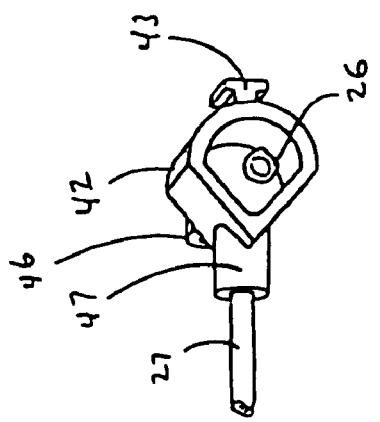
FIG. 3 is a broken perspective view of the sample chamber of the first embodiment of the invention.

The proximal actuation handle 12 includes a shaft 30 having a transverse slot 32 and a spool 34 slidably mounted on the shaft and having a transverse bar (not shown) extending through the slot 32, as is common in the art. The actuation handle 12 is provided with a pinch valve 45 which regulates irrigation and aspiration and a sample catch assembly 41 which includes a sample chamber 42 and a sample catch member 44. Turning to FIGS. 2 and 3, the sample chamber 42 includes irrigation connectors 46, 47 which couple the first irrigation coupling tube 24 to the second irrigation coupling tube 25. The sample chamber 42 also includes first and second aspiration connectors 48, 49 which couple the first aspiration coupling tube 26 to the second aspiration coupling tube 27. As shown in FIG. 3, the diameter of the chamber 42 is significantly larger than the diameter of the first (and second) aspiration coupling tubes 26 (,27). As also shown in FIG. 3, the chamber 42 includes a sample catch connector 43 for removably coupling the chamber to a distal portion of the shaft 30. The sample catch connector 43 is preferably T-shaped for mating with a slot (not shown) on the shaft 30, but may be otherwise shaped for connection to the shaft. Referring to FIGS. 3 through 5, the sample catch member 44 includes a handle portion 52, an engagement portion 54 which removably engages the sample catch member 44 to the sample chamber 42, and a screen 56. The screen 56 extends through the sample chamber 42 between the first and second aspiration connectors 48, 49. The screen 56 includes a front side 58 and a back side 60 and is provided with a plurality of perforations 62 which are preferably frustoconical in shape and expand from the front side 58 to the back side 60. As further shown in FIGS. 3 through 5, the engagement portion 54 and the opening of the sample chamber 42 preferably have irregular shaped cross-sections which enable the engagement of the engagement portion 54 into the sample chamber 42 in one orientation only. As a result, the frustoconical perforations 62 of the screen 56 can be easily aligned in the proper front to back orientation.

As shown in FIG. 2, the first irrigation coupling tube 24 and the first aspiration coupling tube 26 extend through the pinch valve 45 which operates to control the flow of fluid through the tubes 24, 26. The pinch valve is biased to clamp closed the first irrigation coupling tube 24 and the first aspiration coupling tube 26, i.e, to collapse the tubes on top of each other. Pressing downward on the pinch valve 45 with a practitioner's finger counters the bias of the pinch valve to permit fluid flow through the first irrigation coupling tube 24 and the first aspiration coupling tube 26.

Figure 6:
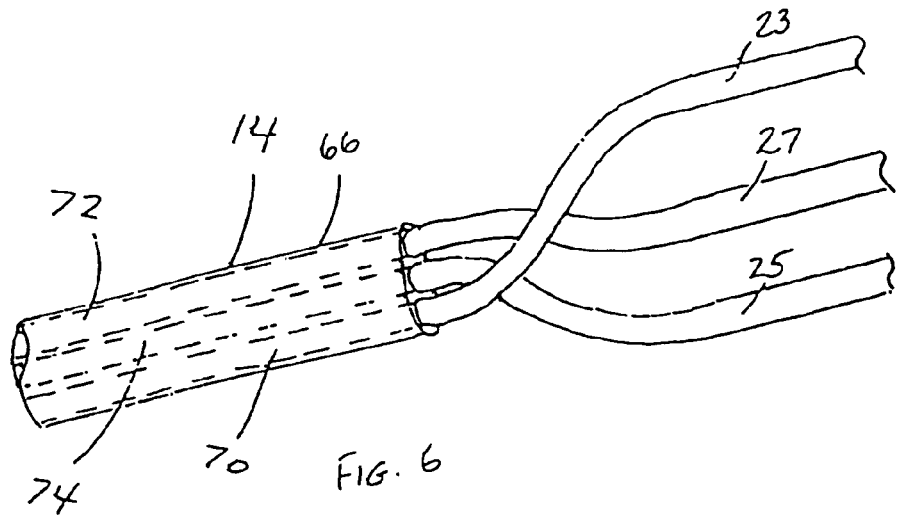
FIG. 6 is an enlarged broken perspective view of the tubular member of the first embodiment of the invention.
Figure 7:
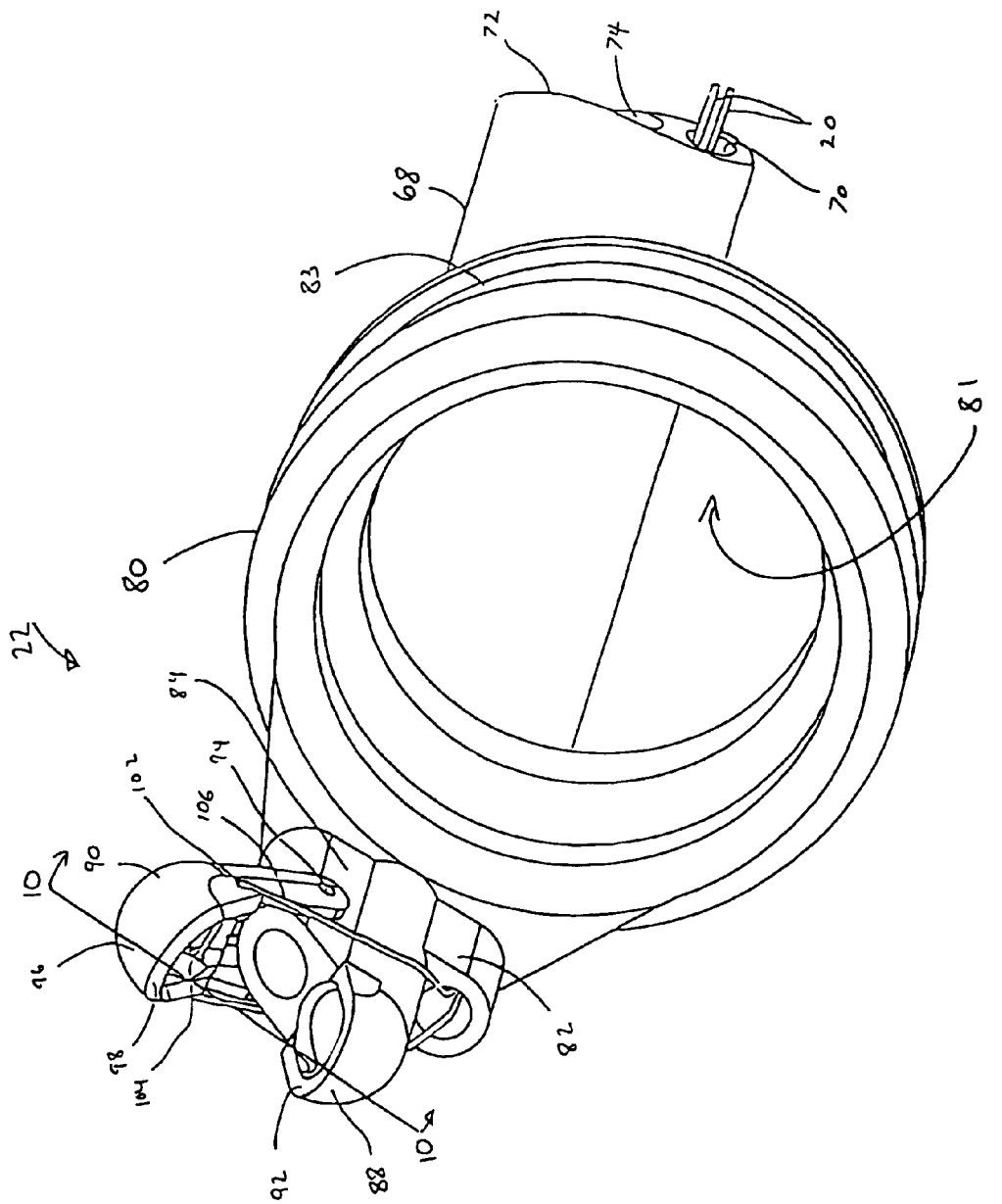
FIG. 7 is an enlarged broken perspective view of the distal assembly of the first embodiment of the invention with the jaws in an open position.

Turning to FIGS. 6 and 7, and in accord with the first embodiment of the invention, the tubular member 14 is preferably an ovoid multi-lumen extrusion. The tubular member includes a proximal end 66, a distal end 68, a control conduit 70, an irrigation conduit 72, and an aspiration conduit 74, each of which extends through the tubular member to the distal assembly 22. At the proximal end 66 of the tubular member, the control conduit 70 is coupled to the control coupling tube 23, the irrigation conduit 72 is coupled to the second irrigation coupling tube 25 and the aspiration conduit 74 is coupled to the second aspiration coupling tube 27.

Figure 8:
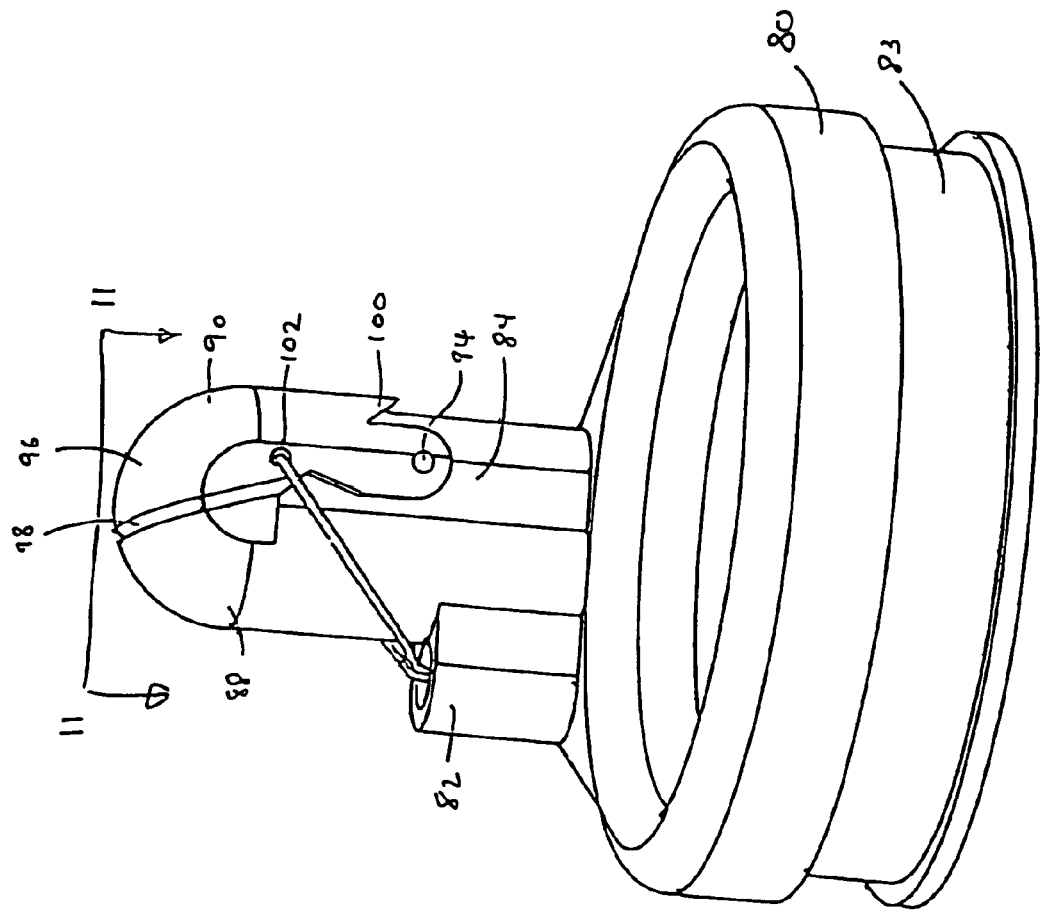
FIG. 8 is an enlarged broken perspective view of the distal assembly of the first embodiment of the invention with the jaws in a closed position.
Figure 9:
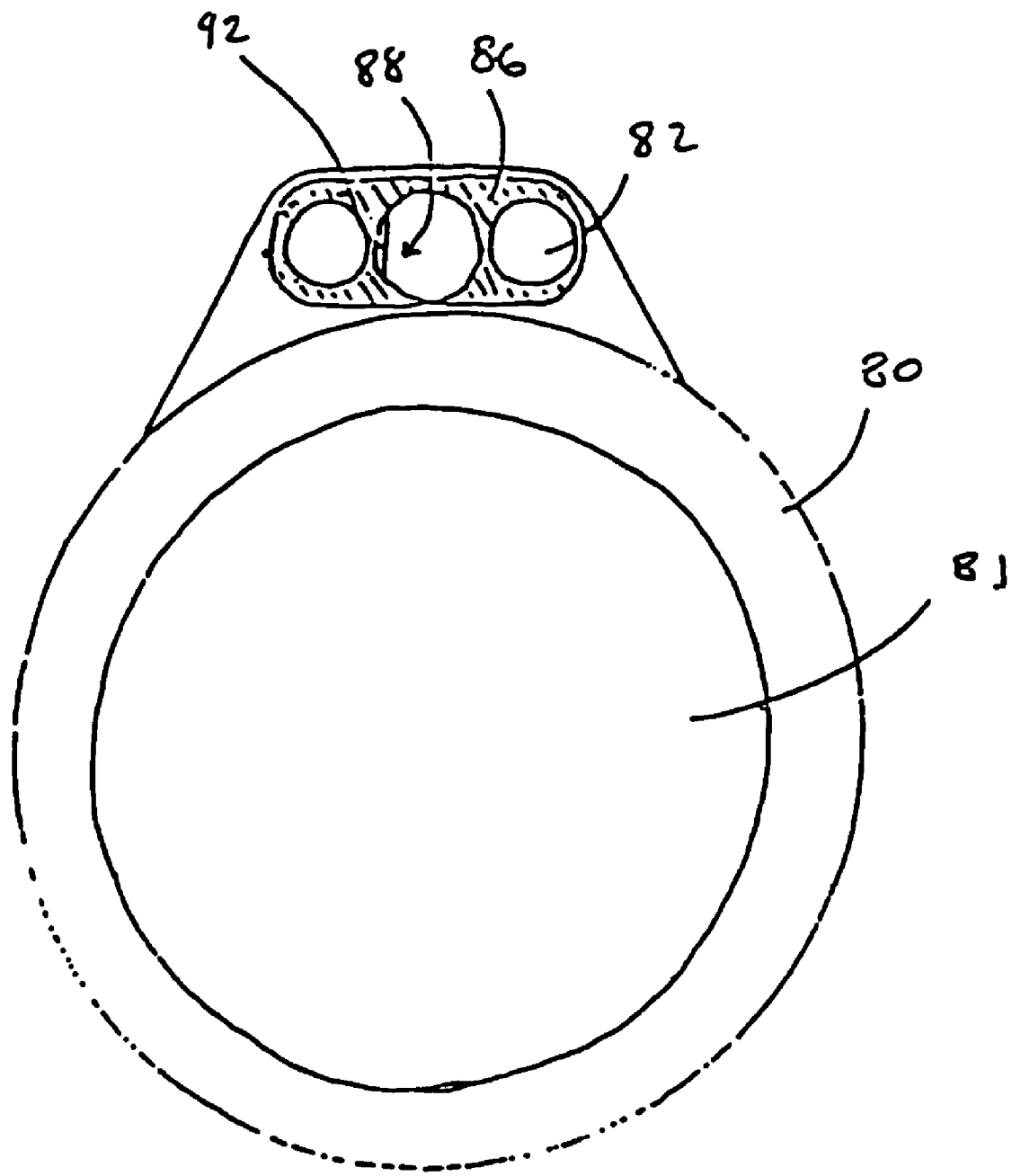
FIG. 9 is a bottom end view of FIG. 8.

Referring to FIGS. 7 through 9, the distal assembly 22 includes a substantially rigid molded collar 80 and a hollow movable jaw 90. The collar 80 is preferably made from a unitary piece of polycarbonate, a glass-filled polycarbonate, a hard grade styrene, or other plastic, while the movable jaw 90 is preferably made from cast metal. The collar includes a central opening 81, a circumferential channel 83, a distally extending control passage 82, a distally extending hollow jaw mount 84, a distally extending hollow stationary jaw 88, and a proximal socket 86. The central opening 81 of the collar 80 is of similar diameter to the outer diameter of the endoscope and is designed to couple the collar to the outside of the distal end of an endoscope. The circumferential channel 81 receives a portion of a silicone rubber sock (not shown), which is used to secure the collar 80 to the endoscope.

The stationary jaw 88 preferably includes a blunt edge or lip 92. The movable jaw 90 is pivotally mounted at a pivot 94 on the jaw mount 84 and is pivotable relative to stationary jaw 88. The movable jaw 90 is preferably provided with a sharp cutting edge 98, a stop 100 for limiting the extent to which the movable jaw pivots away from the stationary jaw 88, and two jaw holes 102, 104, for receiving a pull wire 20, as described below.

Figure 11:
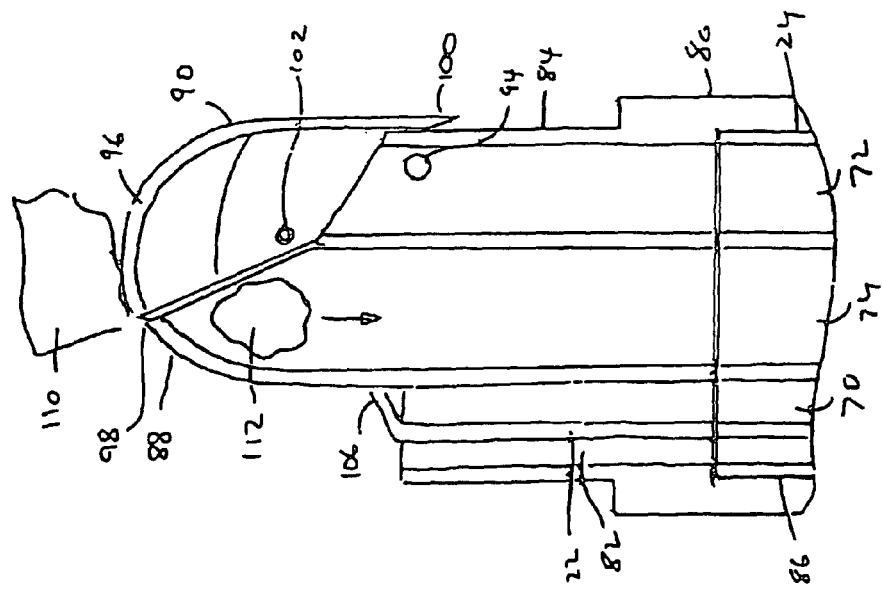
FIG. 11 is cross section across line 11-11 of FIG. 8.
Figure 10:
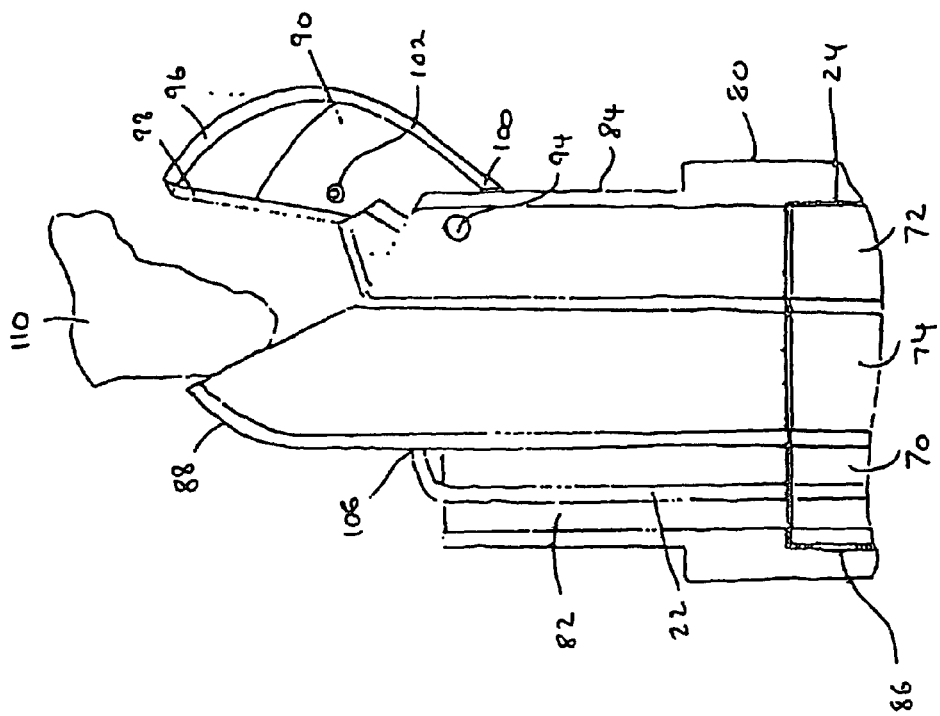
FIG. 10 is a cross section across line 10-10 of FIG. 7.
Figure 14:
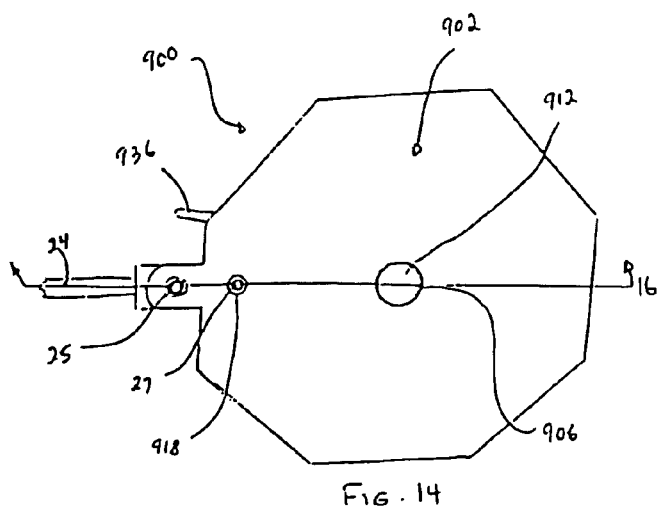
FIG. 14 is a front elevation view of a sample catch assembly according to a second embodiment of the invention.
Figure 17:
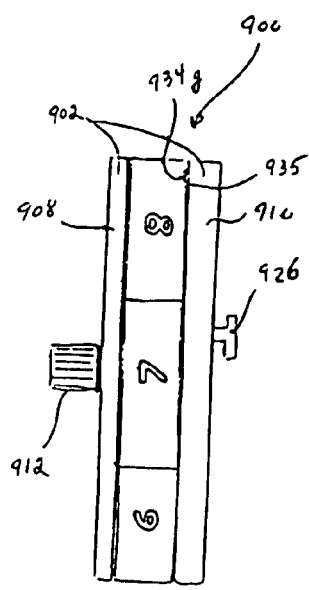
FIG. 17 is a side elevation view of the sample catch assembly according to the second embodiment of the invention.
Figure 15:
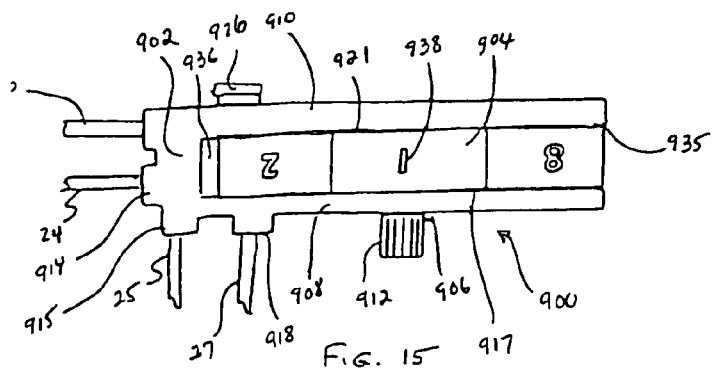
FIG. 15 is a top view of the sample catch assembly according to the second embodiment of the invention.

Referring to FIGS. 9 through 11, the proximal socket 86 is aligned with the control passage 82, the jaw mount 84 and the stationary jaw 88, and is designed to receive the distal end 68 of the flexible tubular member 14. The distal end 68 of the tubular member is secured in the proximal socket 86, preferably using an adhesion bonding agent, such that the control passage 82 is coupled to the control conduit 70, the jaw mount 84 is coupled substantially fluidtight to the irrigation conduit 72, and the stationary jaw 88 is coupled substantially fluidtight to the aspiration conduit 74.

Turning back to FIGS. 1, 6, 7 and 10, a central portion of the pull wire 20 extends through the jaw holes 102, 104 and the ends of the pull wire 20 extend through the control passage 82, the control conduit 70, and the control coupling tube 23 to the spool 34. Referring to FIG. 12, alternatively the pull wire 20a forms a secure loop 106a through the jaw holes 102a, 104a by doubling back on itself and forming a twist 108a. Referring to FIG. 13, in yet another alternative, two pull wires 20b, 21b may be used, the distal end of each pull wire being coupled to a jaw hole 102b, 104b by a Z-bend 110b, 112b and extending through the control passage 82b.

Referring to FIGS. 1, 7, and 8, it will be appreciated that movement of the spool 34 relative to the shaft 30 results in movement of the pull wire 20 relative to the tubular member 14 and consequently moves the movable jaw 90 relative to the stationary jaw 88 such that the jaws open (FIG. 7) and close (FIG. 8). Referring to FIGS. 7 through 11, when the stationary and movable jaws 88, 90 are in a closed position a substantially fluidtight passage is formed there between. Because the stationary jaw 88 is coupled to the aspiration conduit 74 and the movable jaw 90 is coupled over the irrigation conduit 72, a substantially fluidtight coupling of the irrigation and aspiration conduits is achieved.

In use, it will be appreciated that the distal end of the endoscope to which the collar 80 is coupled is maneuvered adjacent the desired tissue for sampling and the distal assembly is brought into contact with tissue 110 (FIGS. 10 and 11). The actuation handle 12 is actuated to close the jaws 88, 90 and cut off a tissue sample 112. When the jaws 88, 90 are in a closed position, the irrigation means and the aspiration means are activated and the first proximal irrigation coupling tube and the first proximal aspiration coupling tube 24, 26 are released from the clamping action of the pinch valve 45 by depressing the pinch valve. Irrigating fluid is thereby permitted to flow through the first and second proximal irrigation coupling tubes 24, 26, through the irrigation conduit 72 and the hollow jaw mount 84, and to the jaws 88, 90 at the distal end of the instrument. The fluid flows through the jaws and is aspirated back to the proximal end of the instrument such that the sample held within the jaws is aspirated with the water.

Turning back to FIGS. 2 through 6, as the water is aspirated through the aspiration conduit 74 and into the sample chamber 42, the sample is filtered onto the screen 58. The frustoconical shape of the perforations 62 permits increased fluid flow through the perforate screen while preventing the tissue sample from passing through the screen. Irrigation and aspiration means are interrupted by releasing the pinch valve 45 such that the pinch valve clamps down on the first proximal irrigation and aspiration coupling tubes 24, 26 and causes the tubes to collapse on top of each other. The screen 58 may easily be removed to retrieve the sample by gripping the handle portion 52 of the sample catch member 44 and pulling the sample catch member from the sample chamber 42. The sample is-recovered from the screen, and the sample catch member is reinserted into the sample chamber to continue the procedure. It will be further appreciated that the entire procedure of cutting a sample and retrieving the sample may be performed without removing the endoscopic multiple sample biopsy forceps instrument from its location within the body. Unlimited subsequent samples may be obtained in an identical manner.

A second embodiment of the proximal actuation handle is also provided, substantially similar to the first embodiment. Referring to FIGS. 14 to 18, the second embodiment has an alternate sample catch assembly 900 able to receive and keep separate samples without necessitating the removal of a sample catch between each sample retrieval. The sample catch assembly 900 generally includes a sample tray holder 902 having front and rear walls 908, 910, a sample tray 904 situated in the tray holder between the front and rear walls, and a threaded connector 906 extending through the front wall 908 of the tray holder 902 and the tray 904 and removably threaded into the rear wall. The tray 904 is rotatable about the threaded connector 906 and relative to the tray holder 902. The threaded connector preferably includes an enlarged head 912 for easier manipulation by a practitioner's fingers.

The front wall 908 of the tray holder 902 includes a first bore 916 (see FIG. 16) through which extends the threaded connector 906, an inside surface 917, and a first aspiration connector 918 which extends through the front wall 908 to the inside surface 917. The rear wall 910 is provided with a second bore 920, preferably threaded, into which the threaded connector 906 is secured, and a sample catch connector 926 which removably couples the sample catch assembly 900 to a distal portion of the shaft 30. The rear wall is also provided with an inside surface 921, a second aspiration connector 922, and a proximal aspiration conduit 924 extending from the inside surface 921 to the second aspiration connector 922. The tray holder 902 is also preferable provided with irrigation connectors 914, 915 which couple the first irrigation coupling tube 24 to the second irrigation coupling tube 25.

Figure 18:
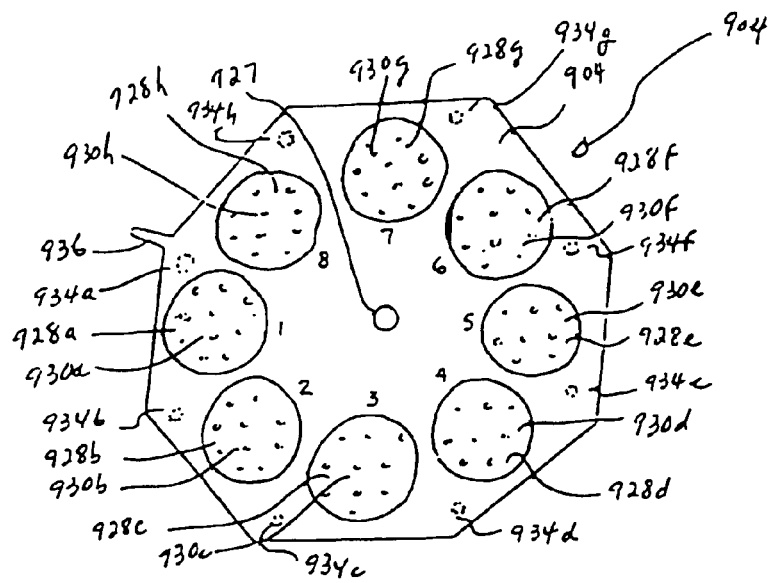
FIG. 18 is a front elevation view of the sample tray of the sample catch assembly according to the second embodiment of the invention.
Figure 16:
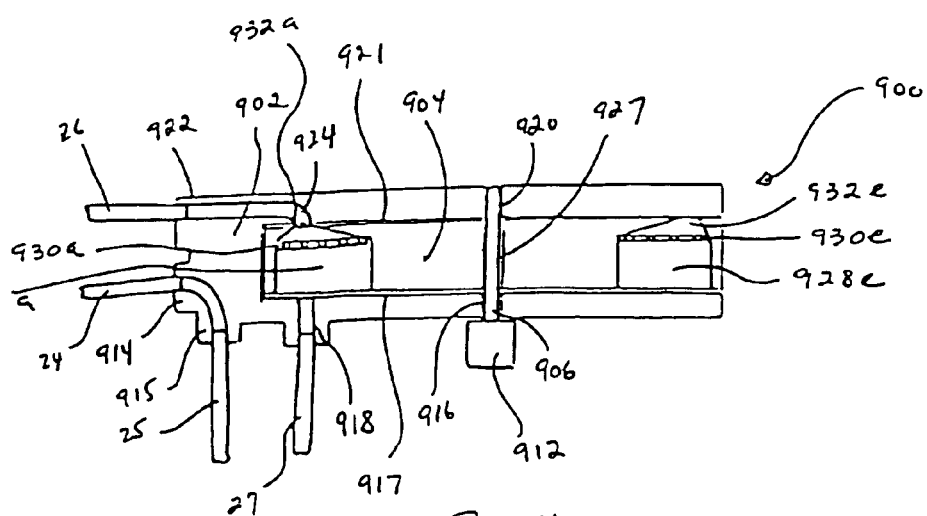
FIG. 16 is cross section view through line 16-16 in FIG. 14.

The tray 904, preferably polygonally shaped, includes an axial bore 927 and a plurality of chambers or cups 928a-h (indexed 1 through 8, respectively, in FIG. 18). Referring to FIGS. 16 and 18, each cup 928a-h has a filter or screen 930a-h and tapers to an outlet 932a-h (932a, 932e shown in FIG. 16) proximal of the screen. The screen preferably has frustoconical perforations. The tray 904 is rotatable within the tray holder 902 such that each of the cups 928a-h is positionable between the first aspiration connector 918 and the proximal aspiration conduit 924 for receiving a tissue sample. The cups 928a-h are maintained in position by providing indentations 934a-h in the tray 904 which receives a protruberance 935 on the inside surface 921 of the rear wall 910 (see FIGS. 15 and 17); i.e., a cup (for example, 928a) is held is position until sufficient force is provided to the tray 904 to rotate the tray and thereby position the next cup (for example, 928b) for receiving a tissue sample. Each of the cups may thereby be positioned to receive a tissue sample without necessitating the removal of a screen between retrieving individual tissue samples. Alternatively, or in conjunction with the indentations 934a-h and the protruberance 935, a ratchet mechanism (not shown) can be provided to prevent rotation of a tray opposite to a predetermined direction. Preferably a stop 936 is also provided on the tray 904 to prevent the tray from being rotated through more than one cycle without first retrieving the samples received in the cups; i.e., to prevent contamination of an earlier retrieved sample by a later retrieved sample. The tray is also preferably provided with indicia 938 to indicate to the practitioner which cup is currently positioned to receive a sample.

After an individual sample has been received into a first cup, according to a similar method as described above with respect to the first embodiment, the aspiration and irrigation are interrupted and the tray 904 is rotated such that the next cup is positioned between the first aspiration connector 918 and the proximal aspiration conduit 924. The process is repeated after each sample is received into a cup. Once the practitioner has obtained all of the desired samples, or once each cup of the tray contains a sample, the threaded connector 906 is uncoupled and the tray is removed and the samples may be removed from the cups of the tray. Index numbers adjacent the cups indicate the order in which the samples were retrieved.

Figure 20:
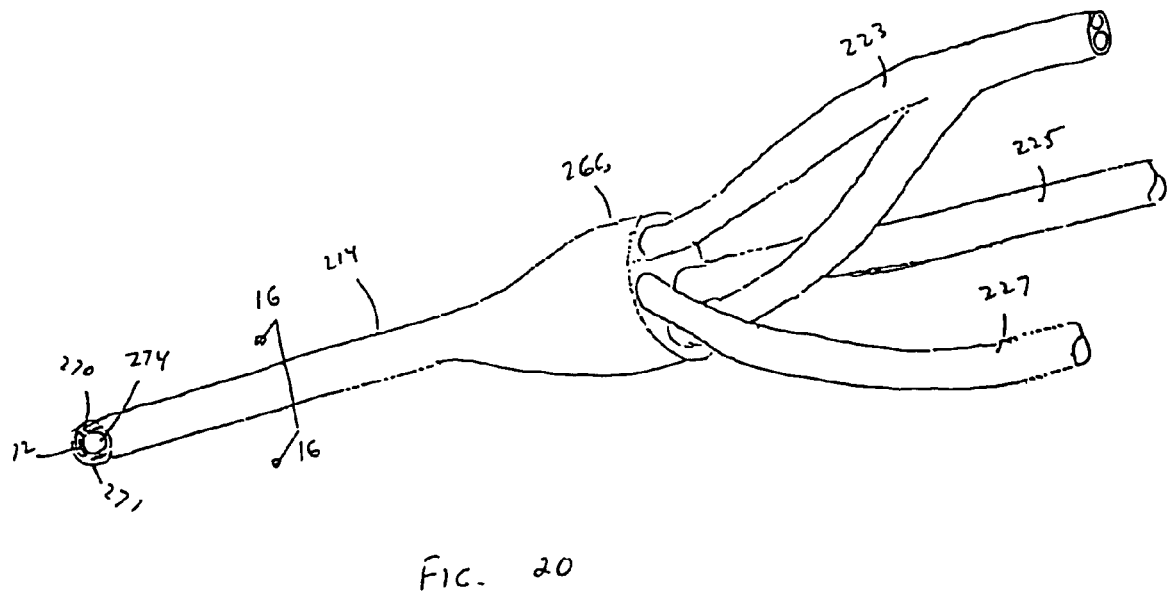
FIG. 20 is an enlarged broken transparent perspective view of the tubular member of the third embodiment of the invention.
Figure 19:
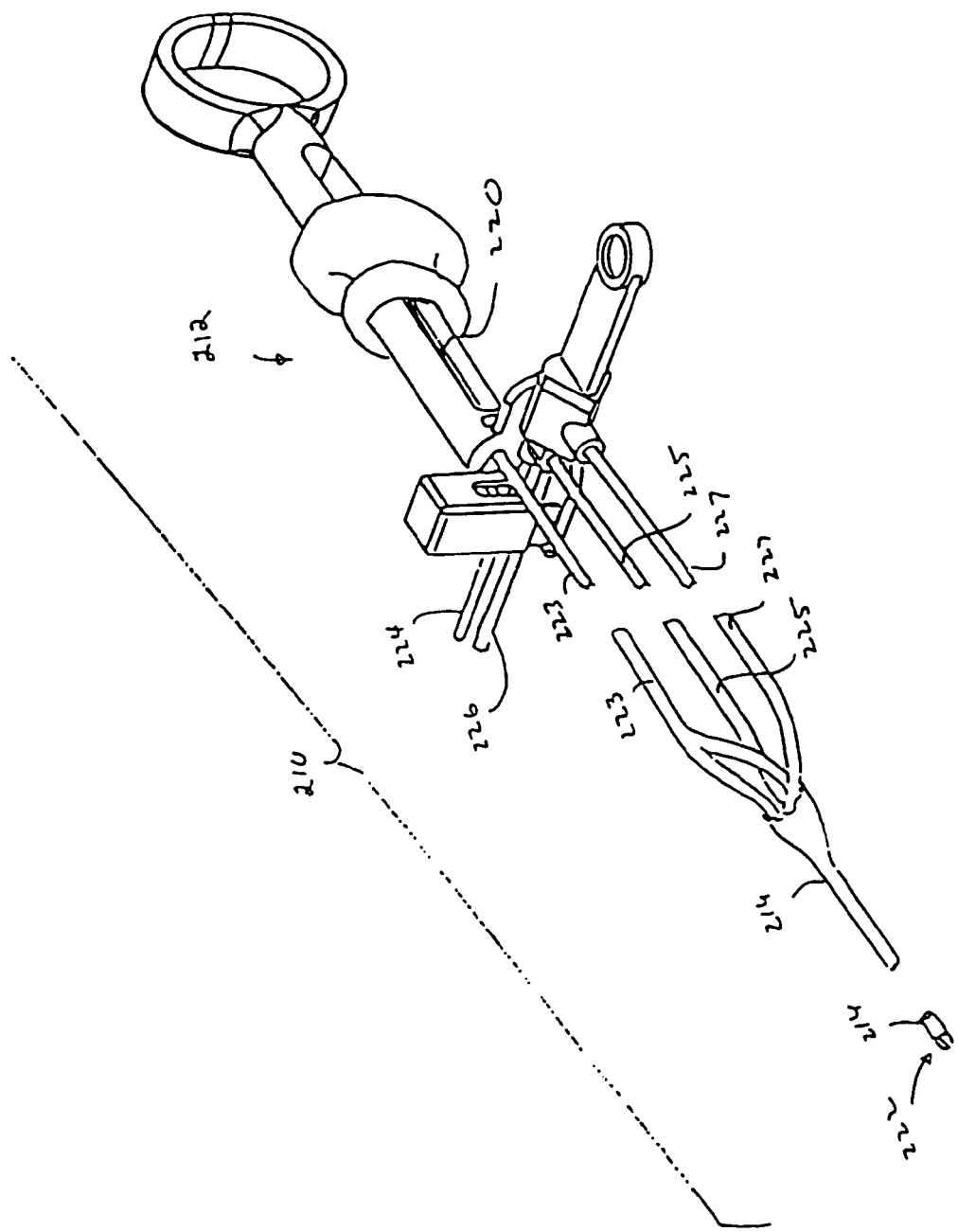
FIG. 19 is a broken perspective view of a third embodiment of an endoscopic biopsy forceps instrument of the invention.

Turning to FIGS. 19 and 20, a third embodiment of a multiple sample biopsy forceps instrument 210 is shown. The instrument includes a proximal actuation handle 212, a flexible multi-lumen tubular member 214, a pull wire 220, and a distal assembly 222. Several coupling tubes are preferably provided to couple the proximal actuation handle 212 to the tubular member 214 and to irrigation and aspiration means. In particular, a Y-shaped control coupling tube 223, first and second irrigation coupling tubes 224, 225, and first and second aspiration coupling tubes 226, 227 are provided.

Figure 21:
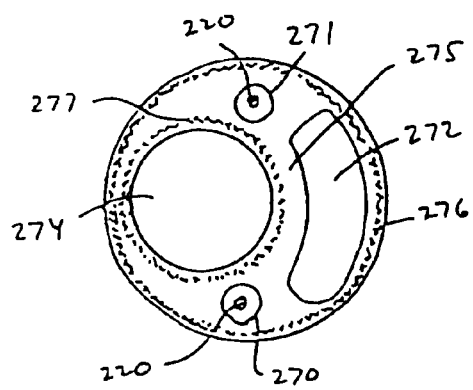
FIG. 21 is an enlarged cross section across line 21-21 of FIG. 20.
Figure 22:
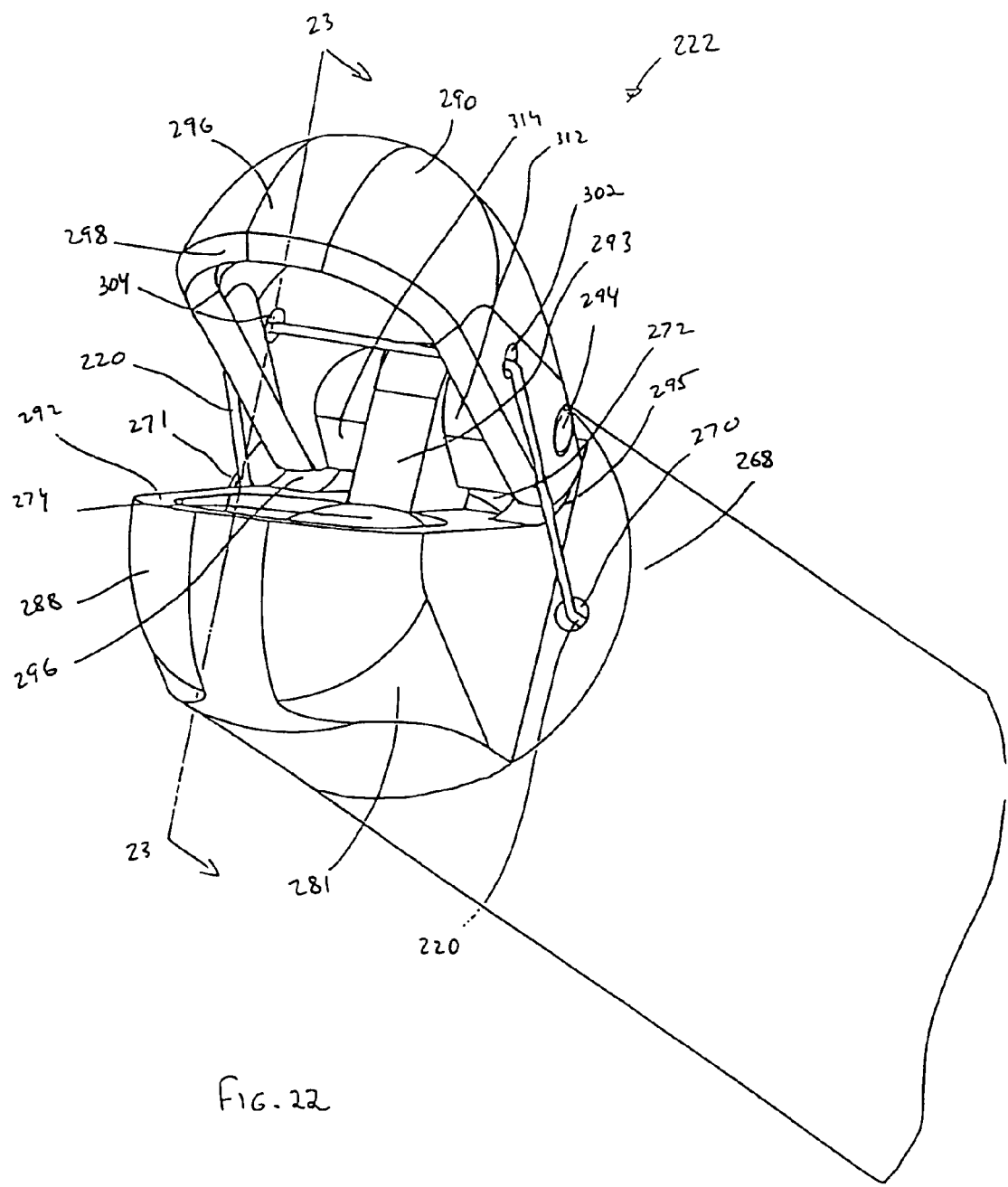
FIG. 22 is an enlarged broken perspective view of the distal assembly of the third embodiment of the invention with the jaws in an open position.

The proximal actuation handle 212 is substantially similar to the first embodiment (with like parts having numbers incremented by 200). Referring to FIGS. 20, 21 and 22, the tubular member 214 is preferably a multi-lumen multi-layer extrusion, and preferably includes a first metal braid 276 beneath the outermost layer to add desired stiffness to the tubular member. If desired, a second metal braid 277 may be additionally provided around the aspiration conduit 274 to stiffen and support the aspiration conduit 274. The tubular member 214 has a proximal end 266, a distal end 268, two control conduits 270, 271, an irrigation conduit 272, and an aspiration conduit 274, each of the conduits 270, 271, 272, 274 extending through the tubular member to the distal assembly 222. The aspiration conduit 274 has a substantially circular cross section. The irrigation conduit 272 has a generally kidney-shaped cross section and is separated from the aspiration conduit 274 by a membrane 275. The control conduits 270, 271 are preferably situated one on either end of the membrane 275.

Referring to FIGS. 22 through 25, the distal assembly 222 according to the third embodiment of the invention includes a stationary jaw 281 coupled, preferably by adhesion bonding, to the distal end 268 of the tubular member. The stationary jaw 281, preferably made of plastic, includes a jaw cup 288, an integral central clevis 293 and integral proximal ramps 295, 296. The jaw cup 288 is located over the aspiration conduit 274 and preferably has a blunt cutting surface or lip 292. The central clevis 293 and proximal ramps 295, 296 extend from the stationary jaw 281 and abut and partially cover the irrigation conduit. A movable jaw 290, preferably made of metal, is provided with a sharp cutting edge 298, defines two jaw holes 302, 304 for receiving a pull wire 220, and is provided with two bosses 312, 314 for mounting the jaw. The bosses 312, 314 loosely engage the central clevis 293 and a pivot pin 294 extends through the bosses and the central clevis. The ramps 295, 296 of the stationary jaw 281 guide the movable jaw 290 when opening and closing and assist to form a substantially fluidtight passage between the movable jaw 290 and the stationary jaw cup 288 when the jaws are in a closed position. A central portion of the pull wire 220 which is perpendicular to the longitudinal axis of the instrument extends through the jaw holes 302, 304 and the ends of the pull wire extend into the control conduits 270, 271. Turning back to FIG. 20, the Y-shaped coupling tube 223 facilitates alignment of the ends of the pull wire 220 for coupling the pull wire to the proximal actuation handle. The pull wire 220 may be coated, e.g., in a plastic, to inhibit the pull wire from cutting into the tubular member.

Figure 23:
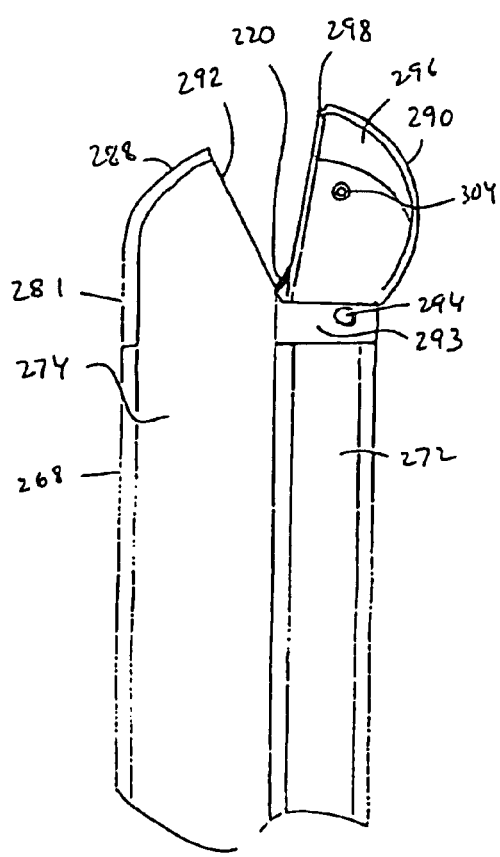
FIG. 23 is a cross section across line 23-23 of FIG. 22.
Figure 25:
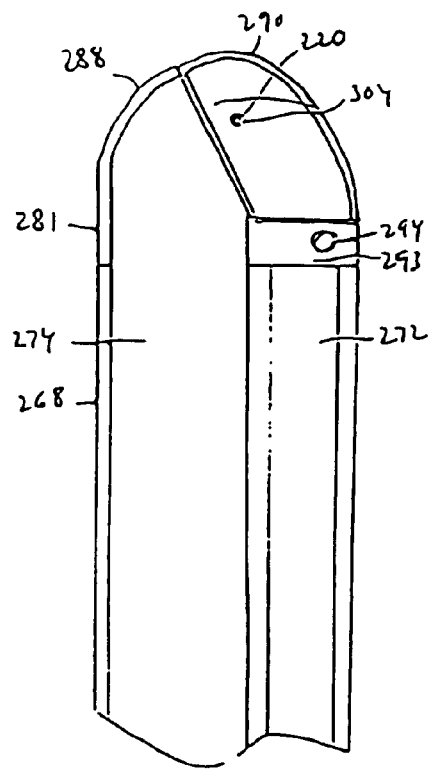
FIG. 25 is a cross section across line 25-25 of FIG. 24.

Referring to FIGS. 23 and 25, the distal end 268 of the tubular member is inserted through the lumen of an endoscope to a biopsy site. The jaws 288, 290 are moved into a closed position cutting off a tissue sample and further providing a substantially fluidtight coupling between the irrigation and aspiration conduits 272, 274. While it appears from the illustrations of FIGS. 23 and 25 that the irrigation conduit 272 is obstructed at the distal end by clevis 293, it will be appreciated that the irrigation conduit 272 is substantially wider than the clevis and that fluid may flow around the clevis to the aspiration conduit 274.

Figure 27:
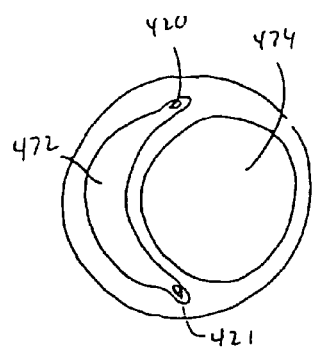
FIG. 27 is an enlarged cross-section across line 27-27 of FIG. 26.
Figure 26:
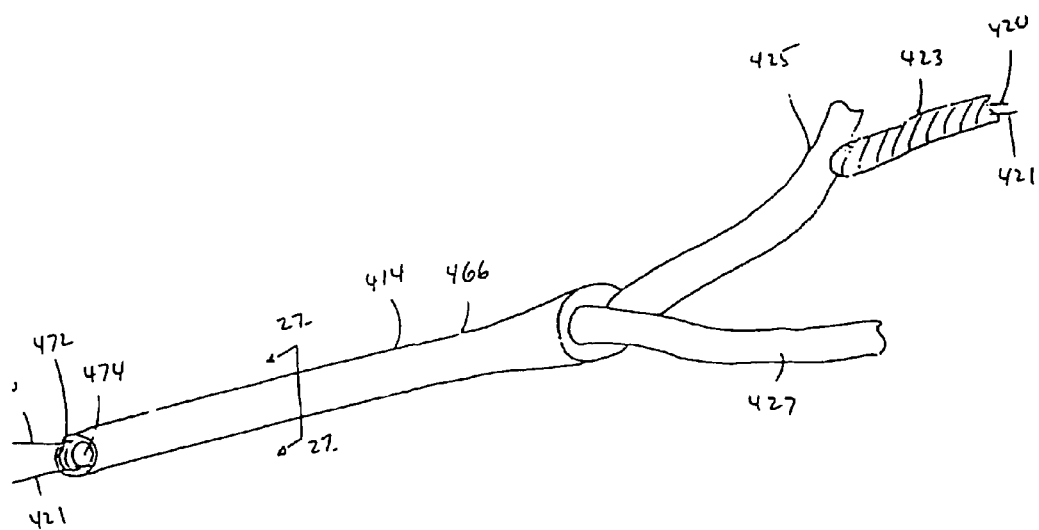
FIG. 26 is an enlarged broken transparent perspective view of the tubular member of the fourth embodiment of the invention.
Figure 28:
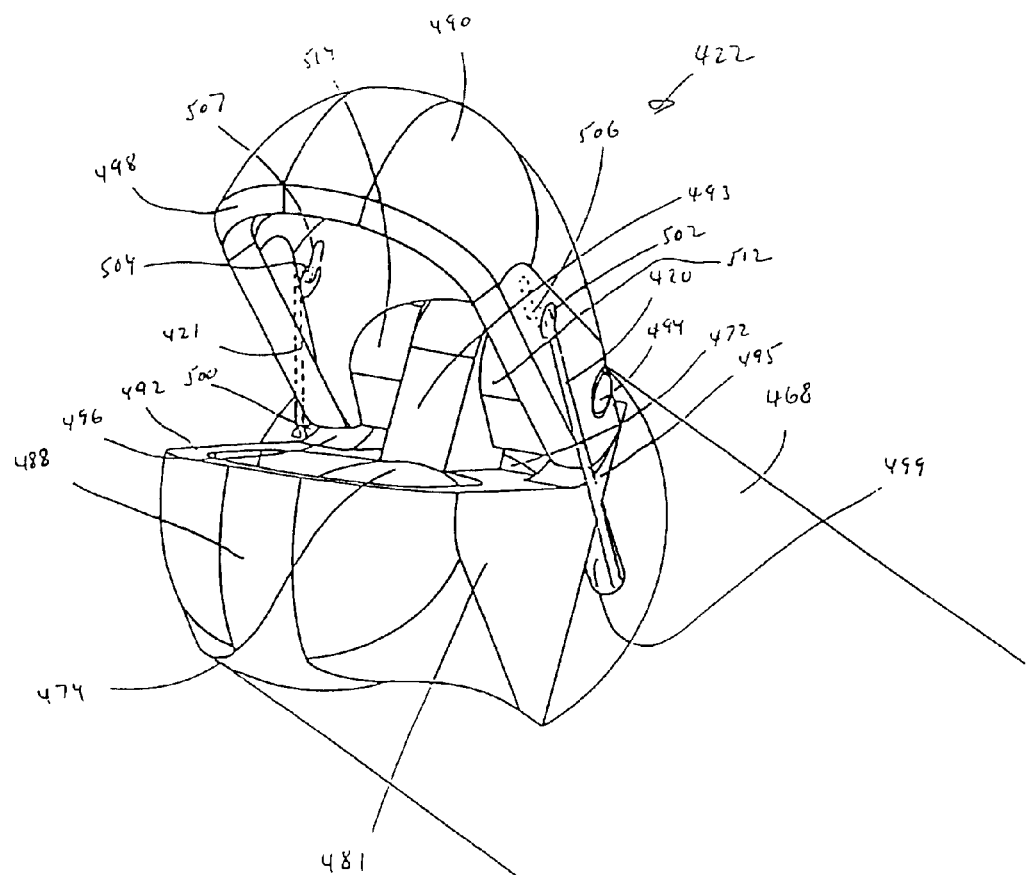
FIG. 28 is a enlarged broken perspective view of the distal end of a fourth embodiment of the invention with the jaws in an open position.

Turning now to FIGS. 26 through 28, a fourth embodiment of a multiple sample biopsy forceps, substantially similar to the third embodiment (with like parts having numbers incremented by another 200) is shown. The tubular member 414 has a proximal end 466, a distal end 468, an irrigation conduit 472, and an aspiration conduit 474. The aspiration conduit 474 has a substantially circular cross section, while the irrigation conduit 472 has a generally crescent-shaped cross section. A control coupling tube 423 is coupled to the second irrigation coupling tube 425. Two pull wires 420, 421 extend through the control coupling tube 423, pass through a substantially fluidtight valve (not shown) coupling the control coupling tube 423 and the second irrigation coupling tube 425, enter into the second irrigation coupling tube 425, and extend through the irrigation conduit 472 to the distal end 468 of the tubular member. An aspiration coupling tube 427 is coupled to the aspiration conduit 474.

Referring to FIG. 28, the distal assembly 422 of the fourth embodiment of the invention includes a stationary jaw 481 bonded to the distal end 468 of the tubular member, and a movable jaw 490 coupled thereto. The stationary jaw 481 includes a jaw cup 488, an integral central clevis 493, and ramps 495, 496. The jaw cup abuts the distal end of the tubular member and is positioned over the aspiration conduit 474 and preferably has a blunt cutting surface or lip 492. The central clevis 493 and ramps 495, 496 extend from the stationary jaw 481 and abut and partially cover the irrigation conduit 474. A movable jaw 490, preferably made of metal, is provided with a sharp cutting edge 498, defines two jaw holes 402, 404 for receiving a pull wire 420, and is provided with two bosses 512, 514 for mounting the jaw. The bosses 512, 514 loosely engage the central clevis 493 and a pivot pin 494 extends through the bosses and the central clevis. By partially covering the irrigation conduit, the ramps form entrances 499, 500 for the pull wires. The movable jaw 490 rides on the proximal ramps 495, 496 when moving from an open to a closed position. The pull wires 420, 421 are coupled to the jaw holes 502, 504 by a Z-bend 506, 507 and extend through the entrances 499, 500 into the irrigation conduit 472, through a portion of the second irrigation coupling tube 425, and further into a control coupling tube 423 coupled thereto. The entrances 499, 500 are sufficiently small that only an insubstantial amount of fluid exits from the irrigation conduit when the jaws are in a closed position and irrigant is forced through the irrigation conduit 474 to the distal assembly.

Figure 29:
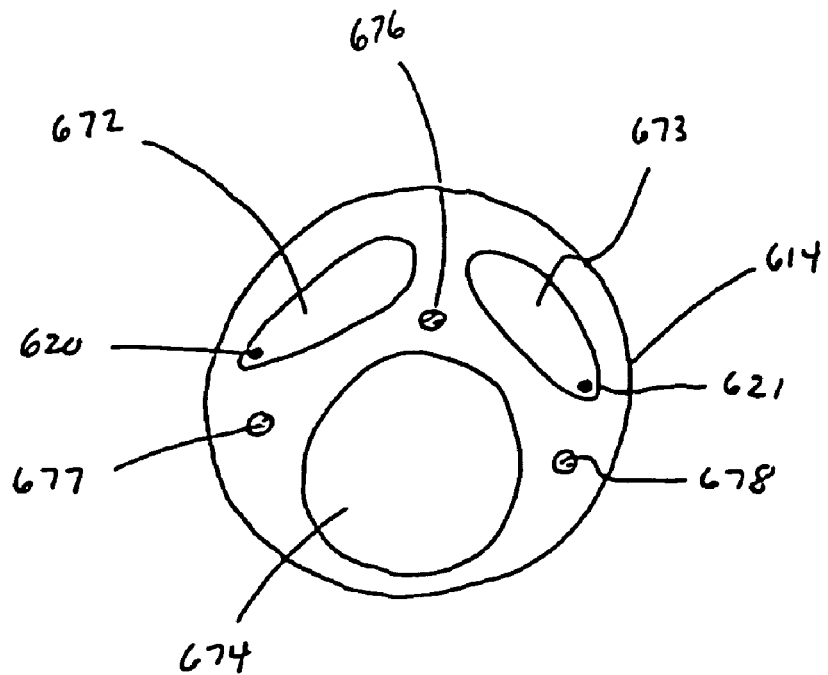
FIG. 29 is a cross-section of a tubular member according to a fifth embodiment of the invention.

Turning to FIG. 29, a fifth embodiment of the invention, substantially similar to the fourth embodiment (with like parts having numbers incremented by 200) is shown. The tubular member 614 is preferably a multi-lumen extrusion co-extruded with support wires 676, 677, 678. The tubular member 614 has two irrigation conduits 672, 673, and an aspiration conduit 674. The aspiration conduit 674 has a substantially circular cross section, and the irrigation conduits 672, 673 have a generally ovoid cross section. The extrusion is preferably made of a polymer (e.g., polyurethane, a polyether block amide, polyethylene, or PVC) or another bondable material. A pull wire 620, 621 extends through each irrigation conduit 672, 673. By way of example, the preferred diameter for the tubular member 614 is approximately 2.8-3.3 mm, the preferred diameter for the aspiration conduit 674 is approximately 1.5 mm, and the preferred diameter for each of the support wires 676, 677, 678 is approximately 0.4 mm. The support wires are preferably made of stainless steel and are also preferably round, but alternatively may be flat. The tubular member of the fifth embodiment is incorporated into the invention in a manner substantially similar to the tubular member of the fourth embodiment and several advantages are realized with this embodiment. First, a three support wire co-extrusion provides necessary rigidity to the wall of the aspiration conduit. Second, the three wire co-extrusion is easy to manufacturer.

Figure 30:
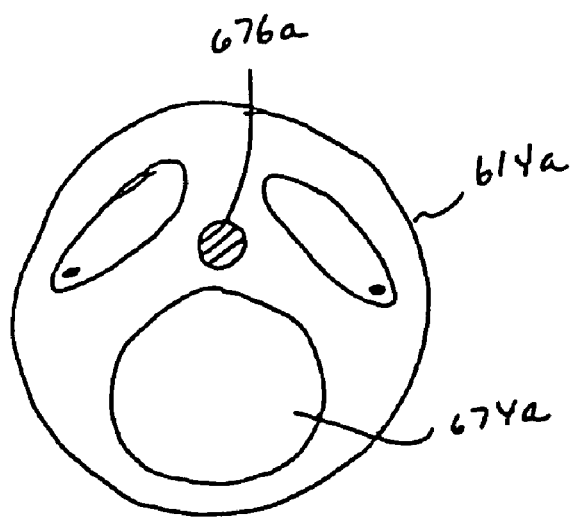
FIG. 30 is a cross-section of a tubular member according to a sixth embodiment of the invention.

Turning to FIG. 30, it will be further appreciated that the three support wires may be replaced with a single larger high tensile support wire 676a or multiband cable through the tubular member 614a. The support wire is preferably located substantially between the two irrigation conduits and the aspiration conduit. The single support wire 676a provides necessary support to the aspiration conduit 674a and is also easy to manufacture. Moreover, the entire support wire or just its distal end may be made from a shape memory material, e.g., Nitinol, which will bend in a predetermined manner when heated to a predetermined temperature. As a result, by heating the support wire to a predetermined temperature, e.g., by applying a current thereto, the shape memory distal end of the support wire can be made to bend in a predetermined manner and consequently the tubular member can be made to bend in a predetermined manner. Tissue samples can thereby be retrieved which are not linearly aligned with the endoscope through which the distal end of the biopsy forceps instrument extends.

There have been described and illustrated herein several embodiments of a multiple sample endoscopic biopsy instrument. While particular embodiments of the invention have been described, it is not intended that the invention be limited thereto, as it is intended that the invention be as broad in scope as the art will allow and that the specification be read likewise. Therefore, while a particular manner of coupling the proximal actuation handle to the tubular member has been disclosed for the several embodiments, it will be appreciated that other manners of coupling the proximal and distal assemblies may be used as well. In addition, while a pinch valve is described for regulating aspiration and irrigation through the tubular member, it will be appreciated that other valve means may likewise be used to the same effect. Also, it will be appreciated that separate valve means may be provided to individually control aspiration and irrigation. It will also be appreciated that while the valve means has been shown coupled to the proximal actuation handle, the valve means may be separable and/or independent from the proximal actuation handle. Furthermore, while the chamber has been described as being removably coupled to the shaft, it will be appreciated that the chamber may be integral with the shaft or, alternatively, not coupled to the actuation handle. Moreover, the shapes of the chamber and the catch member may be different from that described. In addition, it is not necessary to provide first and second irrigation connectors as a single uninterrupted coupling tube may extend from the irrigation conduit of the tubular member through the valve means. Furthermore, while a spool and shaft type actuation means has been disclosed which moves the pull wire(s) relative to the tubular member, it will be appreciated that the actuation means may be of another type well known in the art. For example, a laparoscopic type handle (scissor-type) may also be used. It will therefore be appreciated by those skilled in the art that yet other modifications could be made to the provided invention without deviating from its spirit and scope as so claimed.

We claim:

1. A medical instrument comprising:
    an elongated member having distal and proximal ends;
    a proximal handle coupled to the proximal end of the elongated member;
    a distal assembly coupled to the distal end of the elongated member; and
    a collar coupled to the distal assembly proximate to the distal assembly;
the collar adapted to couple the distal assembly to a medical instrument, wherein the collar is integrally molded with a portion of the distal assembly; wherein the distal assembly includes a stationary jaw; and wherein the collar is disposed proximally of a proximal end of the stationary jaw.

2. A medical device according to claim 1, wherein the distal assembly includes a moveable jaw, and wherein the moveable jaw is pivotable relative to the stationary jaw.

3. A medical device according to claim 2, wherein a portion of the distal assembly and the collar are composed of a unitary piece of polycarbonate, a glass-filled polycarbonate, a hard grade styrene, or other plastic.

4. A medical device according to claim 3, wherein the movable jaw is composed of metal.

5. A medical device comprising:
    an elongated member having distal and proximal ends;
    a proximal handle coupled to the proximal end of the elongated member;
    a distal assembly coupled to the distal end of the elongated member; and
    a collar coupled to the distal assembly proximate to the distal assembly;
the collar adapted to couple the distal assembly to a medical instrument, wherein the collar includes a proximal socket for receiving the distal end of the elongated member, wherein the proximal socket is aligned with the distal assembly, wherein the elongated member is secured in the proximal socket such that the elongated member is coupled to at least one portion of the distal assembly, and wherein the elongated member is adhesion bonded to the proximal socket.

6. A method of coupling a medical instrument to a medical device comprising:
    providing a medical device include an elongated member having distal and proximal ends, a proximal handle coupled to the proximal end of the elongated member, a distal assembly coupled to the distal end of the elongated member, and a collar coupled to the distal assembly proximate to the distal assembly; and
    coupling the collar to an outside of a distal end of a medical instrument, wherein the collar is integrally molded with a portion of the distal assembly; and wherein the distal assembly includes a stationary jaw.

7. A method of claim 6, wherein the distal assembly includes a moveable jaw, and wherein the moveable jaw is pivotable relative to the stationary jaw.

8. A method of claim 7, wherein a portion of the distal assembly and the collar are composed of a unitary piece of polycarbonate, a glass-filled polycarbonate, a hard grade styrene, or other plastic.

9. A method of claim 8, wherein the movable jaw is composed of metal.

* * * * *

UNITED STATES PATENT AND TRADEMARK OFFICE
CERTIFICATE OF CORRECTION

| | |
|---|---|
| PATENT NO. | : 7,833,167 B2 |
| APPLICATION NO. | : 11/725549 |
| DATED | : November 16, 2010 |
| INVENTOR(S) | : Juergen Kortenbach |

It is certified that error appears in the above-identified patent and that said Letters Patent is hereby corrected as shown below:

Column 13, line 25, "medical instrument" should read --medical device--.

Column 13, line 39, "moveable" (both occurrences) should read --movable--.

Column 14, line 23, "medical device include" should read --medical device that includes--.

Column 14, line 34, "moveable" (both occurrences) should read --movable--.

Signed and Sealed this
First Day of March, 2011

David J. Kappos
*Director of the United States Patent and Trademark Office*